United States Patent [19]

Marciniak et al.

[11] Patent Number: 5,698,696

[45] Date of Patent: Dec. 16, 1997

[54] PROCESS FOR PREPARING 2,3-DIHYDRO-BENZOFURANOL DERIVATIVES

[75] Inventors: Gilbert Marciniak, Dachstein, France; Richard A. Schnettler, Cincinnati, Ohio; Timothy A. Ayers, Loveland, Ohio; Damian J. Krysan, Cincinnati, Ohio

[73] Assignee: Hoechst Marion Roussel, Inc., Cincinnati, Ohio

[21] Appl. No.: 612,366

[22] Filed: Mar. 7, 1996

[30] Foreign Application Priority Data

Mar. 10, 1995 [EP] European Pat. Off. .............. 95400518

[51] Int. Cl.$^6$ ...................... C07D 405/06; C07D 307/81; C07D 307/83

[52] U.S. Cl. ................ 544/376; 544/153; 546/196; 548/525; 549/462; 549/466; 549/467; 549/468; 435/126

[58] Field of Search ...................... 435/126; 549/462, 549/466, 467, 468; 544/153, 376; 546/196; 548/525

[56] References Cited

FOREIGN PATENT DOCUMENTS 0483772  5/1992  European Pat. Off. .
20057   10/1993 WIPO .

OTHER PUBLICATIONS

Chemical Abstracts, vol. 119, No. 25, Abstract No. 270991k, Dec. 20, 1993.

The J. of Organic Chemistry, vol. 57, No. 19, pp. 5271–5276, Sep. 11, 1992—John C. Gilbert et al.

Primary Examiner—Bernard Dentz
Attorney, Agent, or Firm—Carolyn D. Moon

[57] ABSTRACT

This invention relates to a novel process for preparing 2,3-dihydro-benzofuranol derivatives and to the novel intermediates produced thereby.

13 Claims, No Drawings

PROCESS FOR PREPARING 2,3-DIHYDRO-BENZOFURANOL DERIVATIVES

BACKGROUND OF THE INVENTION

This invention relates to a novel process for preparing 2,3-dihydro-benzofuranol derivatives and to the novel intermediates produced thereby.

The 2,3-dihydro-benzofuranol derivatives manifest the property of being free radical scavengers. Disease conditions capable of being ameliorated by free radical scavengers are, for example, stroke, nervous system trauma or reperfusion damage as more fully described in Patent Application WO 93/20057, filed Mar. 10, 1993 and U.S. counterpart U.S. Ser. No. 08/318,633, U.S. filing date Dec. 22, 1994, which is incorporated herein by reference.

More specifically this invention relates to novel process for preparing 2,3-dihydro-benzofuranol derivatives of the formula (I)

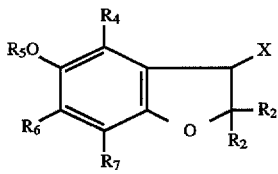

(I)

including the stereoisomers, enantiomers, optically active and racemic mixtures thereof, or their pharmaceutically acceptable salts thereof, wherein $R_2$ is $C_{1-4}$ alkyl each $R_2$ moiety being independently $C_{1-4}$ alkyl or both $R_2$ moieties, when taken together with the carbon atom to which they are attached, form a $C_{5-6}$ cyclic hydrocarbyl moiety;
$R_4$ is $C_{1-6}$ alkyl;
$R_5$ is H or C(O)R with R being H or $C_{1-9}$ alkyl;
$R_6$ is $C_{1-6}$ alkyl;
$R_7$ is H or $C_{1-6}$ alkyl;
X is $COOR_8$, $CH_2OH$, halomethyl, C(O)A or $CH_2A$;
A is $NR_7R_9$, $-N^{\oplus}R_6R_6R_6$-$Q^{\ominus}$, pyrrolidino, piperidino, morpholino, or 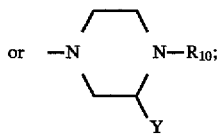

$R_8$ is H, $C_{1-6}$ alkyl, or $-(CH_2)_m$-A with m being 2, 3 or 4;
$R_9$ is H,

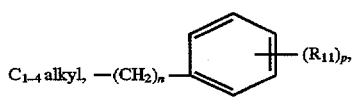

n is 1, 2, 3, or 4, p is 1, 2, or 3;
$R_{10}$ is H, $C_{1-8}$ alkyl, $C_{2-6}$ alkenyl, $C_{4-6}$ cycloalkyl, cyclohexylmethyl, hydroxyalkyl ($C_{2-6}$), dihydroxyalkyl ($C_{3-6}$), $C_{2-9}$ acyloxyalkyl ($C_{2-6}$), $C_{1-4}$ alkoxyalkyl ($C_{1-6}$), $-(CH_2)_{2-6}-O-(CH_2)_{2-4}-OH$,

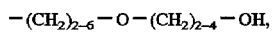

t being 0, 1 or 2, or pyrimidinyl, with the proviso that when Y is other than H then $R_{10}$ is H;
Y is H, $CH_3$ or $COOR_7$;
$R_{11}$ is H, $C_{1-4}$ alkoxy, $C_{1-4}$ alkyl or halogeno;
$R_{12}$ is ortho $C_{1-4}$ alkoxy, ortho $C_{1-4}$ alkyl or p-halo; and
Q is a halide, or sulfonate ion $^{\ominus}$—$SO_3R_1$ with $R_1$ being H, $C_{1-6}$ alkyl, aryl or aralkyl.

SUMMARY OF THE INVENTION

The present invention provides a novel process for preparing benzofuranol derivatives of formula (I)

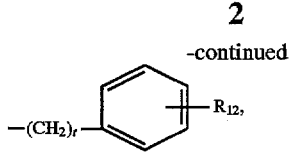

(I)

including stereoisomers, enantiomers, optically active and racemic mixtures thereof, or their pharmaceutically acceptable salts thereof, wherein $R_2$ is $C_{1-4}$ alkyl each $R_2$ moiety being independently $C_{1-4}$ alkyl or both $R_2$ moieties, when taken together with the carbon atom to which they are attached, form a $C_{5-6}$ cyclic hydrocarbyl moiety;
$R_4$ is $C_{1-6}$ alkyl;
$R_5$ is H or C(O)R with R being H or $C_{1-9}$ alkyl;
$R_6$ is $C_{1-6}$ alkyl;
$R_7$ is H or $C_{1-6}$ alkyl;
X is $COOR_8$, $CH_2OH$, halomethyl, C(O)A or $CH_2A$;
A is $NR_7R_9$, $-N^{\oplus}R_6R_6R_6$-$Q^{\ominus}$, pyrrolidino, piperidino, morpholino, or

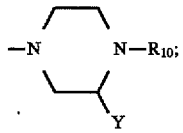

$R_8$ is H, $C_{1-6}$alkyl, or $-(CH_2)_m$-A with m being 2, 3 or 4;
$R_9$ is H, $C_{1-4}$ alkyl,

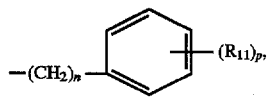

n is 1, 2, 3 or 4, p is 1, 2, or 3;
$R_{10}$ is H, $C_{1-8}$ alkyl, $C_{2-6}$ alkenyl, $C_{4-6}$ cycloalkyl, cyclohexylmethyl, hydroxyalkyl ($C_{2-6}$), dihydroxyalkyl ($C_{3-6}$), $C_{2-9}$ acyloxyalkyl ($C_{2-6}$), $C_{1-4}$alkoxyalkyl ($C_{1-6}$), $-(CH_2)_{2-6}-O-(CH_2)_{2-4}-OH$,

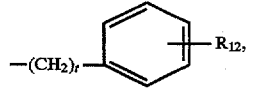

t being 0, 1 or 2, or pyrimidinyl, with the proviso that when Y is other than H then $R_{10}$ is H;

Y is H, CH₃ or COOR₇;
R₁₁ is H, C₁₋₄ alkoxy, C₁₋₄ alkyl or halogeno;
R₁₂ is ortho C₁₋₄ alkoxy, ortho C₁₋₄ alkyl or p-halo; and
Q is a halide, or sulfonate ion ⊖—SO₃R₁ with R₁ being H, C₁₋₆ alkyl, aryl or aralkyl,
comprising the steps of:

(a) reacting a hydroquinone of formula (3) wherein R₄, R₆ and R₇ are defined above and Pg is hydrogen or a suitable protecting group,

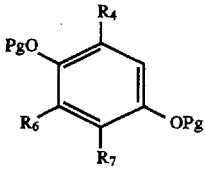
(3)

with a 2-halogeno-2-(C₁₋₄)alkyl(C₁₋₆)acylhalide or a 2-halogeno-2-(C₁₋₄)alkyl(C₁₋₆)acid of formula R₂-C(W)(R₂)C(O)V wherein R₂ is as defined above, W is hydrogen or halogen such as iodide, bromide, chloride or fluoride and more preferably bromide or chloride and V is halogen as defined above or hydroxy (—OH) using Friedel-Crafts reaction conditions, optionally saponifying or deprotecting the so produced compound, thereby producing a benzofuranone of formula (6), wherein R₂, R₄, R₆ and R₇ are as defined above,

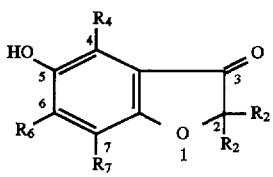
(6)

(b) protecting the 5-hydroxy moiety of so-produced benzofuranone (6) with a suitable protecting group and converting the ketone moiety to exo-methylene moiety thereby producing the benzofuran of formula (8), wherein R₂, R₄, R₆ and Pg are as defined above,

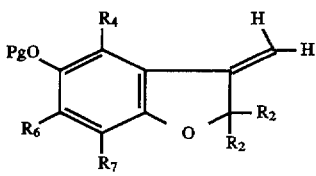
(8)

(c) converting by hydroboration/oxidation the exo-methylene group of the so-produced benzofuran (8) into 3-hydroxymethyl group thereby producing compound of formula (9) wherein R₂, R₄, R₆, R₇ and Pg are as defined above,

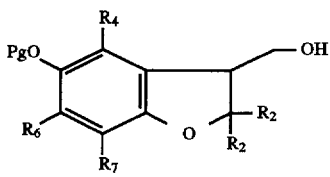
(9)

optionally,
(d) resolving the alcohol (9) to obtain the (R) and (S) optically active compounds (9),
optionally,
(e) deprotecting the 5-hydroxy group of compound (9), thereby producing the benzofuranol of formula (I) wherein X is CH₂OH and R₅ is H, optionally,
(f) oxidizing 3-hydroxymethyl of compound (9) into 3-carboxylic acid of formula (12)

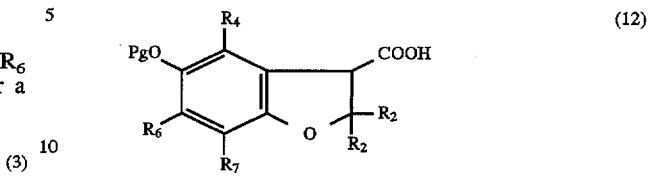
(12)

optionally,
(g) resolving the racemic acid of formula (12) to obtain the (S) and (R) optically active compounds (12),
optionally,
(h) deprotecting the 5-hydroxy group of the acid (12), thereby producing the benzofuranol of formula (I) wherein X is COOH and R₅ is H,
optionally,
(i) esterifying the carboxylic acid of formula (12) and optionally deprotecting the hydroxy group, thereby producing the benzofuranol of formula (I) wherein X is COOR₈ and R₅ is H,
optionally,
(j) reacting a desired amino group with the carboxylic acid of formula (12) and optionally deprotecting the hydroxy group, thereby producing the benzofuranol of formula (I) wherein X is C(O)A and R₅ is H,
optionally,
(k) reducing the carboxylic acid (12) thereby producing compound of formula (9),
optionally,
(l) optionally deprotecting the hydroxy of compound (9) and converting the hydroxy of the 3-hydroxy-methyl group to an halogen, thereby producing the benzofuranol of formula (I) wherein X is halomethyl and R₅ is H,
optionally,
(m) deprotecting optionally the hydroxy group of compound (9) and converting the hydroxy of the 3-hydroxymethyl group to a leaving group, thereby producing the benzofuranol of 15 formula (10),

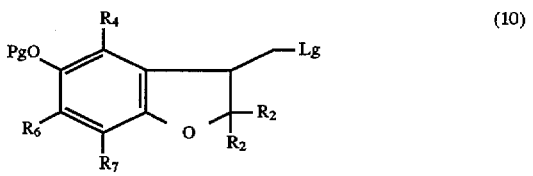
(10)

(n) substituting the leaving group of compound (10) by the desired amino group and deprotecting optionally the hydroxy group to obtain the product of formula (I) wherein X is CH₂A and R₅ is H,
optionally,
(o) esterifying the 5-hydroxy group of compound of formula (I) wherein R₅ is H, to give compound of formula (I) wherein R₅ is COR, R being C₁₋₉ alkyl,
and optionally converting said product to pharmaceutically acceptable salt thereof.

As used herein in this application:
(a) the term "alkyl" means univalent radical (-R). It includes the straight and branched chain saturated aliphatic hydrocarbyl moieties having the indicated number of carbon atoms. For example, the terms "C₁₋₉ alkyl" and "C₁₋₈ alkyl" refer to a saturated straight or branched chain hydrocarbon radicals having from one to nine and one to eight carbon atoms respectively, preferably having one to six ("$C_{1-6}$ alkyl") and, more preferably having one to four carbon atoms ("$C_{1-4}$ alkyl"). Included within the scope of this term are methyl, ethyl, n-propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-hexyl, octyl, 4-methyl-3-heptyl, nonyl and the like. Likewise, $C_{1-6}$ alkyl preferably has $C_{1-4}$ alkyl. All $C_{1-4}$ alkyls, including the foregoing preferences, can have 1, 2, 3, or 4 carbons in any arrangement.

(b) the term "alkylene" means saturated divalent alkane radical (-R-). Likewise the term "alkylene" includes straight or branched-chain moieties. Some examples of branched-chain alkylene moieties are ethylethylene, 2-methyltrimethylene, 2,2-dimethyltrimethylene, and so on. For example, $C_3$ alkylene can mean $$-CH_2-CH_2-CH_2- \text{ or } -\underset{\underset{CH_3}{|}}{\overset{\overset{CH_3}{|}}{C}}- \text{ or } -CH_2-\underset{\underset{CH_3}{|}}{CH}- \text{ or } -\underset{\underset{CH_3}{|}}{CH}-CH_2-;$$

(c) the term "alkenyl" means unsaturated univalent radical. It includes the straight and branched chain unsaturated aliphatic hydrocarbyl moieties having the indicated number of carbons. For example, the term "$C_{2-6}$ alkenyl" refers to an unsaturated straight or branched chain hydrocarbon radical having from two to six carbon atoms. Included in the scope of this term are ethenyl, propenyl, 2-methyl-2-propenyl, butenyl and the like;

(d) the designation —C(O)— or —CO— refers to a carbonyl group of the formula:

<img>carbonyl structure</img>

The term —C(O)R includes those carbonyl moieties wherein R is H or $C_{1-9}$ alkyl moiety, embracing, for example, formyl, methylcarbonyl, ethylcarbonyl, propylcarbonyl, and the like. The term —COOR includes those alkoxycarbonyl moieties wherein R is H or $C_{1-6}$ alkyl moiety embracing, for example, methoxycarbonyl, ethoxycarbonyl, t-butyloxy-carbonyl, and the like. Alkoxycarbonyl wherein R is not H are also called esters;

(e) the $NR_7R_8$ moieties include the amino, mono and di-substituted amines with $R_7$ and $R_8$ being as defined;

(f) the term "Bn" refers to a benzyl functionality of the formula:

<img>benzyl structure</img>

(g) the term "aralkyl" refers to moieties of formula

<img>aralkyl structure —(CH2)m—phenyl—(R)n</img> wherein m=1,2,3 or 4 including benzyl, phenylethyl, phenylpropyl or phenylbutyl moieties; the phenyl moieties of which may bear 1,2,3 substituents selected from the group consisting of $C_{1-4}$ alkoxy (preferably methoxy), $C_{1-4}$ alkyl (preferably methyl) or halogen (preferably chloro but including bromo and iodo) at the position ortho, meta or, para;

(h) the mono and di-hydroxy substituted alkyl moieties are those moieties wherein the alkyl moiety can bear one or two OH groups (other than two hydroxy groups on one carbon atom), preferably moieties bearing a hydroxy group on a terminal carbon atom;

(i) $C_{2-9}$ acyloxy alkylene ($C_{2-6}$) are those compounds wherein the acyloxy moiety has 2 to 9 carbon atoms and the alkylene moiety has 2 to 6 carbon atoms such as exemplified by $-CH_2CH_2-OC(O)CH_3$;

(j) the $-C_{2-6}$ alkylene—O—$(CH_2)_{2-4}$ OH moieties have respectively a divalent 2–6 carbon atom moiety attached to an oxygen (O). The oxygen is also attached to a 2–4 carbon moiety terminating in a hydroxy moiety, one example is $-CH_2CH_2OCH_2CH_2CH_2OH$;

(k) piperidino refers to compound of formula:

<img>piperidino ring structure numbered 2,3,4,5,6 with N</img>

(l) pyrrolidino refers to compound of formula:

<img>pyrrolidino ring structure</img>

(m) piperazino refers to compound of formula:

<img>piperazino ring structure numbered 2,3,4,5,6 with two N</img>

(n) morpholino refers to compound of formula:

<img>morpholino ring structure with N and O</img>

(o) the designation:

<img>hydroquinone structure with OH groups and (R)n</img> refers to hydroquinone, substituted hydroquinone and it is understood that R can be attached in any of the 2,3,5, or 6 positions;

(p) the designation

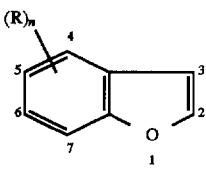

refers to a benzofuran derivatives, substituted benzofuran and it is understood that R can be attached in any of the 2,3,4,5,6, or 7 position; benzofuranol derivative refers to 5-hydroxy-benzofuran derivative; and (q) the designation

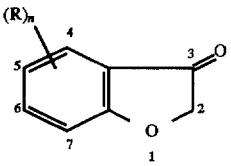

refers to a benzofuranone, substituted benzofuranone and it is understood that R can be attached in any of the 2,4,5,6, or 7 positions.

The designation "————" refers to a bond that protrudes forward out of the plane of the page.

The designation "- - - - - - -" refers to a bond that protrudes backward out of the plane of the page.

The term "pharmaceutically acceptable salts" include those acid addition salts derived by reaction with acids, for example, hydrochloric, hydrobromic, sulfuric, nitric or phosphoric acids and such organic carboxylic acids as acetic, propionic, glycolic, maleic, tartaric, citric, salicylic, 2-acetyloxybenzoic acids or organic sulfonic acids such as methanesulfonic, 4-toluenesulfonic and naphthalenesulfonic acids. Of course other acids well known to the pharmaceutical art may also be utilized. The term "pharmaceutically acceptable salts" may also include hydrates.

Stereoisomers of the compounds of formula (I) is a general term for all isomers of these compounds that differ only in the orientation of their atoms in space. It includes geometric (cis/trans) isomers, and isomers of compounds with more than one chiral center that are not mirror images of one another (diastereomers or diastereoisomers). The term "enantiomer" refers to two stereoisomers that are non superimposable mirror images of one another. The term "chiral center" refers to a carbon atom to which four different groups are attached. The nomenclature R/S is used as described in IUPAC-IUB Joint Commission on Biochemical Nomenclature, Eur. J. Biochem. 138: 9–37 (1984). A chiral material may either contain an equal amount of the R and S isomers in which case it is called "racemic" or it may not contain equal amounts of R and S isomer in which case it is called "optically active", or "nonracemic".

A mixture may be resolved or isolated according to conventional and standard procedures well known in the art, e.g., chromatographic separation on chiral stationary phase, use of optically active esters, fractional crystallization of addition salts formed by reagents used for that purpose, as described in "Enantiomers, Racemates, and resolutions", J. Jacques, A. Collet, and S. H. Wilen, Wiley (1981), enzymatic resolution and the like. Stereoisomer resolution is carried out on the intermediates, or the final products of formula (I). The term "resolution" means separation of a racemic mixture into its optically active components. In addition, enantiomers may be prepared by utilizing enantioselective or asymmetric synthesis which are well known by a person of ordinary skill in the art. The term "enantioselective" or "asymmetric" means the ability to produce a product in an optically active form.

It is understood that the compounds of formula (I) may exist in a variety of stereoisomeric configurations. It is further understood that the compounds of the present invention encompass those compounds of formula (I) in each of their various structural and stereoisomeric configurations as individual isomers or as mixtures of isomers.

The term "enantiomeric excess" or ee refers to the percent by which one enantiomer, E1, is in excess in a mixture of the two enantiomers, E1 plus E2, such that;

$$\frac{(E1-E2)}{(E1+E2)} \times 100\% = ee$$

the term (+)—refers to the plus enantiomer, (−)—refers to the minus enantiomer.

"Pg" means a suitable protecting group. "Protected hydroxy" means protecting group (Pg) attached to the oxygen of the hydroxy group in place of H. Suitable protecting groups can be found in T. W. Greene and P. Wuts, *Protective groups inorganic synthesis*, 2nd. ed., John Wiley & Sons Inc., New York (1991), incorporated herein by reference. For convenience in schemes Pg may also be a hydrogen atom.

Previously, compounds of formula (I) have been synthesized by the process depicted in the following reaction SCHEME I as disclosed in Patent Application WO93/20057, filed Mar. 10, 1993.

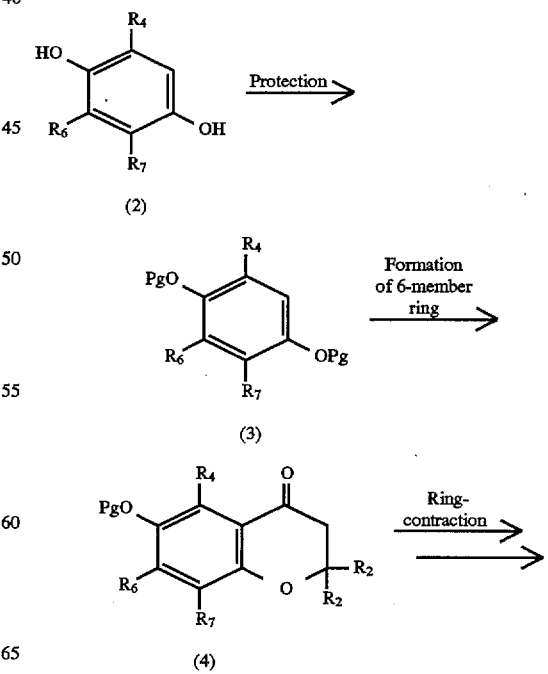

9
-continued
SCHEME I:
Previous synthesis

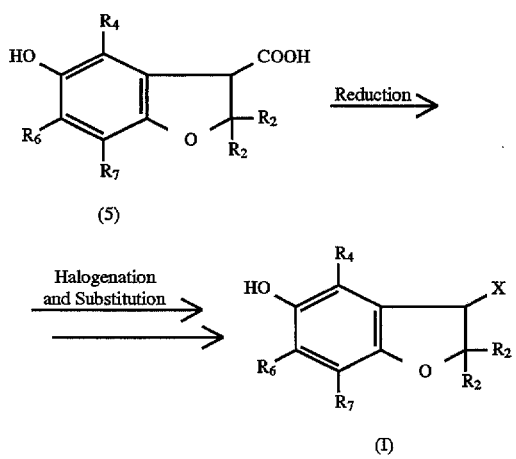

Fries rearrangement of substituted acrylic acid diesters (3) of hydroquinones (2) at elevated temperatures such as 120°–150° C. gives the 6-member ring (protected 6-hydroxy-3,4-dihydro-1,2H-benzopyran-4-one) (4). Ring-contraction of the resulting enolizable ketone with thallium (III)nitrate in trimethylorthoformate/methanol gives compound (5). The acid moiety of (5) is then reduced to its corresponding alcohol, the so-produced alcohol is converted to a halogen which is then substituted by an amino group to give the desired 2,3-dihydro-benzofuranol (I). This synthesis uses in the ring contraction step thallium (III) nitrate salts which have to be handled with great care because of their high toxicity. Moreover, the use of these salts can induce problems of treating the waste, the solvent and all the material contacting the salts. Due to all these inconveniences the large scale preparation of 2,3-dihydro-benzofuranol derivatives may be impractical.

After extensive experimentation, the present invention discloses a new process which circumvents the ring contraction step and the use of thallium(III)nitrate salts. This new process, using a Friedel-Crafts reaction which will be defined, gives the new intermediate 5-member ring (6) from the starting hydroquinone directly instead of the 6-member ring (4) previously obtained SCHEME I. This new intermediate is used to obtain the stereoisomers or the mixture of the 2,3-dihydro-benzofuranol derivatives (I).

Racemate or optically active derivatives may be obtained as depicted in the following SCHEME II.
Scheme II, Step A:

In the present invention the aryl used in the Friedel-Crafts reaction is a substituted hydroquinone of formula (2) wherein $R_4$, $R_6$ and $R_7$ are defined above.

(2)

2,6-dimethylhydroquinone ($R_7$ is hydrogen) and 2,3,5-trimethylhydroquinone are commercially available. Other substituted hydroquinone (2) may be easily synthesized using well known methods in the art such as for example disclosed in "*Methoden der Organischen Chemie*" Houben Weyl, band VII/3a chinone, teil 1 and disclosed by J. T.

10

Gupton et al. (*J. Org. Chem.* 1983, 48, 2933–2936) which are incorporated herein by reference.

Hydroxy groups of the trialkylhydroquinone (2) are optionally protected using suitable protecting groups (Pg) to give protected hydroquinone (3). Many protective groups used usually for alcohols are applicable to phenol. Ethers and esters are the most common protective groups used. Ether means forming an —OR group wherein R is alkyl, such as for example methyl, cyclohexyl, isopropyl, t-butyl, or methoxymethyl, benzyloxymethyl, 2-(trimethylsilyl)-ethoxymethyl, tetrahydropyranyl, allyl, benzyl, or silyl ethers such as trimethylsilyl, t-Butyldimethylsilyl. Ester means forming esters (—OCOR) such as for example an acetate (—OCOCH$_3$), levulinate (CH$_3$COCH$_2$CH$_2$CO$_2$—), pivaloate ((CH$_3$)3CCO$_2$—), benzoate (—OCOC$_6$H5), carbonates such as methyl carbonate (—OCOCH$_3$), aryl carbonate, benzyl carbonate (—OCOCH$_2$C$_6$HS), carbamates (—OCONHR), phosphinates such as dimethylphosphonyl ester ((CH$_3$)$_2$P(O)O—), sulfonates such as methylsulfonate or mesyl (—OSO$_2$CH$_3$) or toluene sulfonate or tosyl (—OSO$_2$C$_6$H$_4$—p—CH$_3$).

SCHEME II

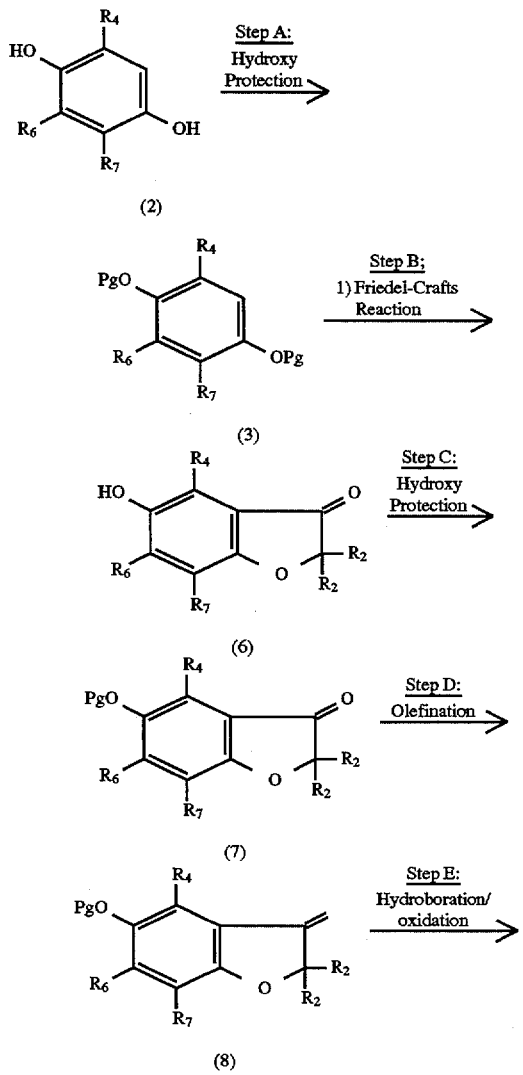

-continued
SCHEME II

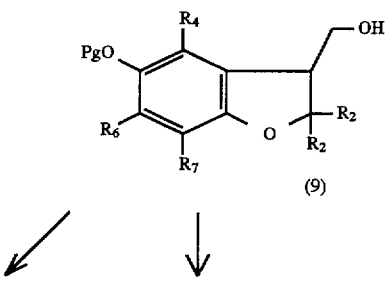
(9)

| SCHEME III | SCHEME IV |
|---|---|
| RACEMATE or OPTICALLY ACTIVE COMPOUNDS by resoloution of the alcohol (9) | OPTICALLY ACTIVE COMPOUNDS by resolution of an acid derived from alcohol (9) |

It is found that the protective groups, may influence the formation of the five member ring. The alkyl groups as protecting groups are preferred and more preferably the methyl group is chosen.

Preferably, the trialkylhydroquinone (2) is protected using a common reaction such as treating trialkyl-hydroquinone (2) with dimethylsulfate or methyliodide in the presence of a base such as potassium carbonate, sodium hydroxide, potassium hydroxide in a solvent such as acetone, alcohols (for example methanol, ethanol) preferably under reflux. The protected hydroquinone (3) is isolated according to well known procedure in the art.

Scheme II, Step B:

The new intermediate (6) is obtained by using a Friedel-Crafts acylation as disclosed in *Methoden der Organischen Chemie* (Houden-Weyl, VII/2a teil I, 1973); or in *Friedel-Crafts and related reactions* (Interscience, New York, 1963–1964), which are incorporated herein by reference. The Friedel-Crafts reaction involves the reaction between an aryl and an acyl halide, a carboxylic acid, an anhydride or a ketene in presence of a catalyst. For the acyi halide all four halides (Cl, Br, I, F) can be used. In the present invention, the reagent to accomplish the formation of (6) is preferably a 2-halogeno-2-($C_{1-4}$)alkyl($C_{1-6}$) acylhalide or a 2-halogeno-2-($C_{1-4}$)alkyl($C_{1-6}$)acid of formula $R_2$-C(W)($R_2$)C(O)V wherein W is hydrogen or halogen such as iodide, bromide, chloride or fluoride and more preferably bromide or chloride and V is halogen as defined above or hydroxy (—OH).

As for example when $R_2$ is methyl or ethyl, respectively the 2-bromo-2-methylpropionic bromide or 2-bromo-2-ethylpropionic bromide are commercially available. When $R_2$ is propyl, commercially available 2-propylpentanoic acid can be converted to a 2-halogeno-2-($C_{1-4}$)alkyl($C_{1-6}$) acid by replacing the α-hydrogen with a halide. More preferably the α-hydrogen is replaced by iodide, bromide or chloride. The "α-hydrogen" means the hydrogen attached to the carbon directly adjacent to the carbonyl function. The α-hydrogen can be replaced by bromide or chloride by well-known methods in the art for example using bromine or chlorine with a phosphorus halide as a catalyst (the reaction is known as the Hell-Volhard-Zelinskii reaction, and chlorosulfuric acid may be also used as a catalyst to obtain the carboxylic acid α-iodinated, as well as chlorinated or brominated), using N-bromosuccinimide or N-chlorosuccinimide and bromic acid or chloric acid. A carboxylic acid may be α-chlorinated using cuprous chloride in polar inert solvents. An acyl chloride can be α-iodinated with iodine and a trace of iodic acid.

The Friedel-Crafts reaction is accomplished most commonly in a solvent such as dichloromethane, dichloroethane, tetrachloroethane, chlorobenzene, nitromethane or carbon disulfide or without any solvent. Catalysts are Lewis acids. "Lewis acids" are species with a vacant orbital. The most common catalysts are ferric chloride, iodine, zinc chloride, aluminium chloride and iron and more preferably aluminum chloride or ferric chloride is used. Preferably the catalyst is used at a ratio of 0.1 to 2 per mole of reagent.

More preferably the hydroquinone (3) is treated with $R_2$—C(halogeno)($R_2$)C(O)halide in a solvent such as dichloromethane, dichloroethane, tetrachloroethane for example in the presence of Lewis acid catalysts (aluminum chloride or ferric chloride) at a range of temperature between –10° C. to 100° C. The so-produced benzofuranone is isolated and optionally deprotected by common methods well known in the art.

A byproduct 1,4-di-(2-halogeno-2-alkyl-alkylacetoxy)-2,3,5-trialkylhydroquinone may be formed during the reaction and the mixture may require a supplemental step of saponification to obtain the desired product. Therefore the mixture is treated by basic conditions such as potassium hydroxide or sodium hydroxide in a mixture of solvent such as aqueous methanol/tetrahydrofuran at a range of temperature of 40° to 80° C. More preferably an aqueous solution of sodium hydroxide is added to the crude product dissolved in methanol/tetrahydrofuran 1/1 and the reaction is conducted at 60° C. for 3 to 5 hours. The new benzofuranone (6) is isolated by standard methods.

Scheme II, Step C:

The 5-hydroxy group of the so-produced benzofuranone (6) is protected. Suitable protecting groups as described previously are used. More preferably reagents such as 2-methyl-proprionylhalide, methylhalide or benzylhalide are used. More preferably 2-methyl-proprionylchloride is added to a solution of benzofuranone (6) in solvent such as for example dichloromethane and the mixture is stirred at a range of temperature between –5° C. to 10° C. under inert atmosphere. The protected compound (7) is isolated by extraction with quantitative yield and can be used without further purification for the next step.

Alternatively, more preferably benzylbromide or benzylchloride is added to a solution of benzofuranone (6) in solvent such as for example acetone, dichloromethane, tetrahydrofuran, dimethylformamide or, dimethylsulfoxide in presence of a base such as potassium carbonate, potassium hydroxide, sodium hydride or, sodium amide. More preferably, benzylbromide is added to a solution of benzofuranone (6) in acetone in the presence of potassium carbonate and the mixture is stirred at a range of temperature of 5° C. to 65° C. The protected compound is isolated by filtration or standard methods well known in the art.

Scheme II, Step D:

The ketone group of the benzofuranone (7) is converted to the exo-methylene group (exo-methylene group means divalent $C_1$ radical which is attached as a side chain rather than included into a ring) using methods known in the art such as for example the method known as the Wittig reaction or a 2-step process involving alkylation with methyl-lithium or a methyl magnesium halide reagent followed by acidic catalyzed elimination of the tertiary alcohol.

In the Wittig reaction ketone group of the benzofuranone (7) is treated with a phosphorus ylid (also called phosphorane which means a substance in which a carbanion is attached to a heteroatom with a high degree of positive charge, i.e. -C⁻-X⁺) to give an olefin as disclosed by Johnson in *Ylid Chemistry* (Academic Press, New York, 1966) which is incorporated herein by reference. Phosphorus ylides are usually prepared by treatment of a phopshonium salt with a base, and phosphonium salts are commercially available or usually prepared from a phosphine and an alkyl halide. Phosphonium salts are most often converted to ylides by treatment with strong bases such as for example butyllithium, sodium or potassium amide, hydride or alkoxide. Solvents such as for example tetrahydrofuran are generally used. The reaction is performed at a range of temperature between −5° C. to 35° C. under inert atmosphere.

More preferably, alkoxide such as for example potassium tert-butoxide is added portionwise at about 0° C. under inert atmosphere to a suspension of benzofuranone (7) and methylphosphonium halide in dry tetrahydrofuran. The mixture is then treated as known in the art to give the product in good yield. The quality of the alkoxide such as potassium tert-butoxide is important to improve the yield of olefin (8).

Alternatively, in the alkylation/elimination process ketone (7) is treated by a methylmagnesium halide such as methylmagnesium chloride, methylmagnesium bromide or methylmagnesium iodide. More preferably, the ketone (7) is treated by methylmagnesium chloride in ether solvents such as for example ether, tetrahydrofuran at a range of temperature from −5° C. to 50° C. to give an intermediate tertiary alcohol. Addition of acid such as concentrated sulfuric acid causes elimination to give the desired olefin (8) which is further purified by well-known methods in the art such as for example by crystallization.

Scheme II, Step E:

Conversion of exo-methylene of (8) in the methyl-alcohol group can be accomplished using hydroboration/oxidation. Olefins are treated with borane in ether solvents. Usually, borane complexes such as with tetrahydrofuran, dimethylsulfide, or tertiary amine which are commercially available are used. Borane can also be prepared in situ by well known methods in the art, by reacting sodium borohydride and boron trifluoride.

More preferably, the olefin (8) is treated with a solution of borane-methyl sulfide complex at about 0° C. under inert atmosphere in solvents such as for example chloroform, dichloromethane, or ethers such as diethylether, tert-budiethylether, tert-butyl methyl ether, tetrahydrofuran. Borane adds to the olefin to form an intermediate which is oxidized. The so-produced organoborane can be oxidized to the primary alcohol (primary alcohol means an alcohol in which the carbon attached to the hydroxy group is linked to one or no alkyl group and at least two hydrogen atoms) with sodium hydroxide-hydrogen peroxide as known in the art. The so-produced alcohol (9) can be utilized without further purification.

Scheme III, Step A:

Optionally, the racemic 3-hydroxymethyl-benzofuran (9) may be resolved or isolated according to conventional and standard procedures well known in the art, e.g., chromatographic separation on chiral stationary phase, use of optically active esters, fractional crystallization of addition salts formed by reagents used for that purpose, enzymatic resolution and the like. More preferably the 3-hydroxymethyl-benzofuran (9) is resolved using enzymatic resolution. More preferably enzymatic transacylation, wherein one enantiomer is reactive and acylated, and the other one remains unchanged, is utilized to resolve the alcohol.

Enzymes generally employed are lipasos from microorganisms like *Candida cylindracea, Rhizopus arrhizus, Chromobacterium viscosum, Pseudomonas cepecia, Mucor miehei* or, *Asperigillus niger*, or from mammalian liver, like porcine pancreatic lipase (PPL), or enzymes from Boehringer Mannhelm Chirazyme L-1, L-2, L-3, L-5, or L-6. The enzyme may be used as a crude extract or in purified form, sometimes entrappod in sepharose or in chromosorb as a solid support. Acylations are run as transesterifications of the alcohol with esters such as for example methyl acetate, acetic anhydride, vinyl acetate, isoprenyl acetate, 2,2,2-trifluoroethyl acetate with the enzyme in organic solvents such as for example ethers such as ether, t-butyl methyl ether, tetrahydrofuran or other solvents such as benzene. More preferably, 3-hydroxymethyl benzofuran (9) is resolved using lipase from *Candida cylindracea* microorganism. More preferably the reaction is performed using vinyl acetate in ether solvent such as for example t-butyl methyl ether at room temperature or a range of temperature from 0° C. to 50° C.

The optically active acetyl derivative of (9) and the unreactive alcohol may be isolated by procedures well known in the art. For example, the mixture is filtered, concentrated under reduced pressure to constant weight and the residue is chromatographed on silica gel to give the acylated isomer and the unchanged isomer. Other methods such as for example HPLC (High Purification Liquid Chromatography) or crystallization may also be used. The acetyl isomer may be deesterified by well known procedures in the art wherein for example the acetyl isomer is dissolved in methanol; and treated by basic conditions such as for example potassium carbonate at a range of temperature from 15° C. to 60° C. The recovered desired optically active alcohol (9) may be purified by procedures well known in the art, such as crystallization.

The undesired optically active alcohol (9) may be recycled one or more times. More preferably, the hydroxy group of the 3-hydroxymethyl is transformed into a leaving group and more preferably into a mesylate by standards methods known in the art. Elimination of the so-produced leaving group leads to the olefin (8) which can be injected into the process. Elimination can be carried out using procedures well known to one of ordinary skill in the art. More preferably, the leaving group is eliminated in basic conditions such as for example potassium tert-butoxide in tetrahydrofuran at room temperature.

The 5-hydroxy of compound (9) may be further deprotected using common methods well known by one skilled in the art. More preferably if isobutyryl has been used to protect the 5-hydroxy, basic conditions such as sodium hydroxide in a mixture of solvents such as water/methanol/tetrahydrofuran can be used at 70° C.–85° C.

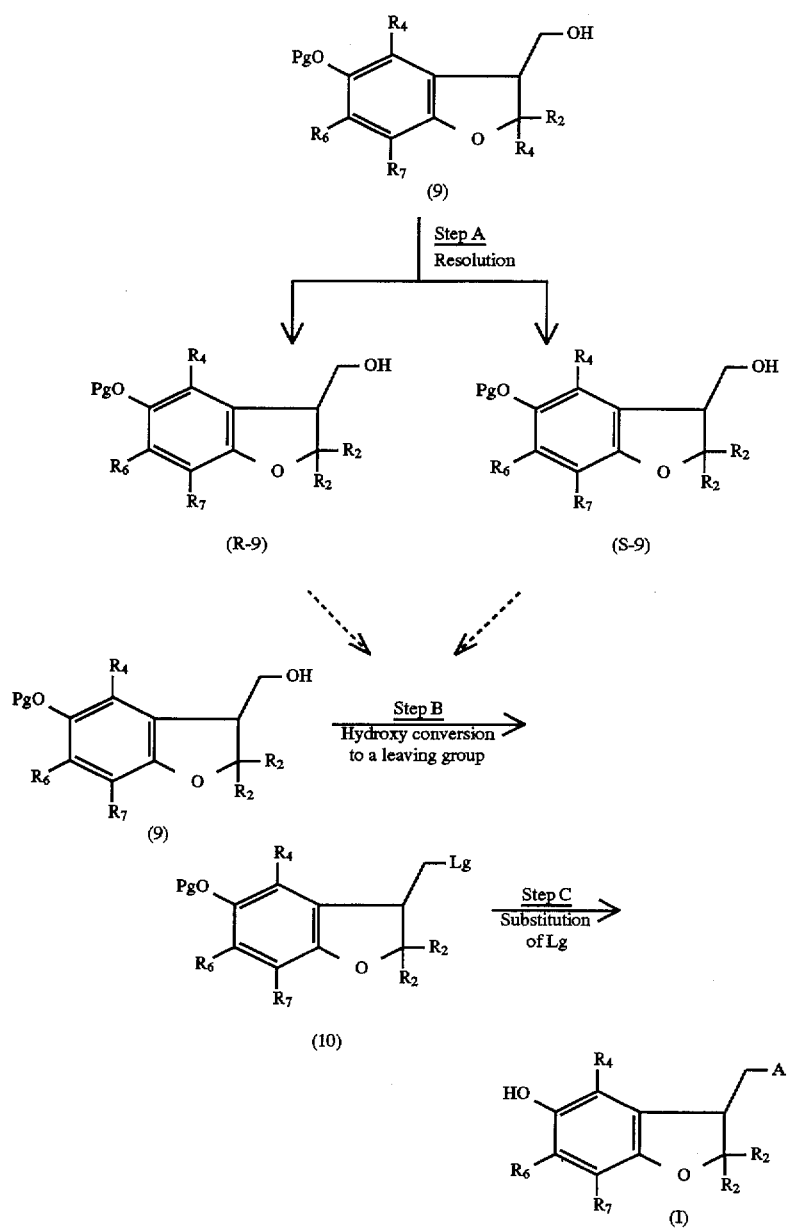

Scheme III, Step B:

The primary alcohol of 3-hydroxymethyl-2,3-dihydrobenzofuran derivative (9) obtained is transformed into a leaving group (Lg) which means a group which can be easily substituted by a nucleophile. Leaving groups are for example tosylate, brosylate, nosylate, mesylate, triflate, nonaflate, tresylate or halides.

More preferably, the hydroxy group is converted into a halide or a mesylate. When the hydroxy group is converted to a halide the most common reagents utilized are for example halogen acids or thionyl halide, phosphorus pentahalide, phosphorus trihalide, phopshoryl halide, trialkyl phopsphorylhalide, triphenylphosphine halide and the like (wherein halide means halogen such as chloride (Cl), bromide (Br) or iodide (I)).

More preferably, the hydroxy group is converted into a bromide by using triphenylphosphine-bromine which is prepared insitu in solvent such as dichtoromethane at a range of temperature from −5° C. to 10° C. The alcohol (9) is added to this mixture at such temperature and then allowed to warm to room temperature. The mixture treated as known in the art gives the product (10) in quantitative yield.

Alternatively, the hydroxy group is converted to a mesylate. The reaction may be performed in basic condition such as in pyridine at room temperature or, more preferably in tetrahydrofuran in presence of a base such as triethylamine at a range of temperature −5° C. to 20° C. for example.

Scheme III, Step C:

To obtain the final compound of formula (I) wherein X is $CH_2A$, A being as defined previously, the leaving group is substituted by the desired amino $-NR_7R_8$, pyrrolidino, piperidino, morpholino or piperazino group.

The desired amines $HNR_7R_8$ are commercially available or easily synthesized using well known methods in the art as for example described in *Comprehensive Organic Chemistry* (Chapter 1.3, Synthesis of amines and ammonium salts, Trost-Flemming, Pergamon Press, 1991), which is incorporated herein by reference. The most common reactions involve reaction between the desired alkyl halide and ammonia:

R—X+NH$_3$→R—NH$_2$+HX

More preferably for the synthesis of a primary amine reduction of an azide obtained by substitution of an alkylhalide or the reaction known as Gabriel reaction, see for example E. F. V. Seeyen and K. Tumbell, *Chem. Rev.* 1988,88, 297 (incorporated herein by reference)involving reaction of a phthalimide ion with an appropriate alkylating reagent and subsequent removal of the phthaloyl group are used. Pyrrolidine, piperidine, morpholine, piperazine and N-methyl piperazine, 2-methylpiperazine, piperazinylformic acid are commercially available.

The substituted piperazine of formula

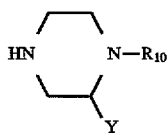

can be easily synthesized by common methods as described above for the amines HNR$_7$R$_8$.

The piperazine of the above formula wherein Y is COOR$_7$ can be easily synthesized by esterifying the commercially available piperazinylformic acid with the desired alkyl reagent by using common esterification methodsbyell known by one ordinary skilled in the art.

The substitution of the leaving group of compound (10) by the desired amino group may be performed by procedures well known in the art such as for example in acetonitrile, dimethyl formamide, methanol, ethanol or isopropanol under reflux temperature. After extraction, the final product (I) can be either isolated using column chromatography or by crystallization. Crystallization seems to give better yield than column chromatography. Optionally the 5-hydroxy group may be deprotected according to well known methods in the art.

The 5-hydroxy protected intermediate (9) may be used to obtain the diastereoisomers R-(I) and S-(I) by resolution of the acid (12) SCHEME IV.

Scheme IV, Step A:

Preferably, the 5-hydroxy group is protected by an alkyl such as methyl or by a benzyl using methods as described previously. The 3-hydroxy moiety of the 3-hydroxymethyl-5-protected hydroxy-2,3-dihydro-benzofuran (9) is oxidized to carboxylic acid to give the compound (12).

Primary alcohols can be oxidized by many strong oxidizing agents such as permanganate, and nitric acid. More preferably, the primary alcohol can be also converted to carboxylic acid in two steps passing through the aldehyde. A common way to obtain the aldehyde is to treat the alcohol with dimethylsulfoxide, dicyclohexyl-carbodiimide (DCC), and anhydrous phosphoric acid. Similar oxidations can be carried out using dimethylsulfoxide and other reagents in place of DCC: acetic anhydride, sulfur trioxide-pyridine-triethylamine, trifluoracetic anhydride, chlorosulfonyl isocyanate, oxalyl chloride, molybdenum peroxide, tosyl chloride, chlorine, bromine, silver tetrafluoroborate and triethylamine, triflic anhydride, potassium iodide and sodium bicarbonate, and methanesulfonic anhydride, among others.

SCHEME IV

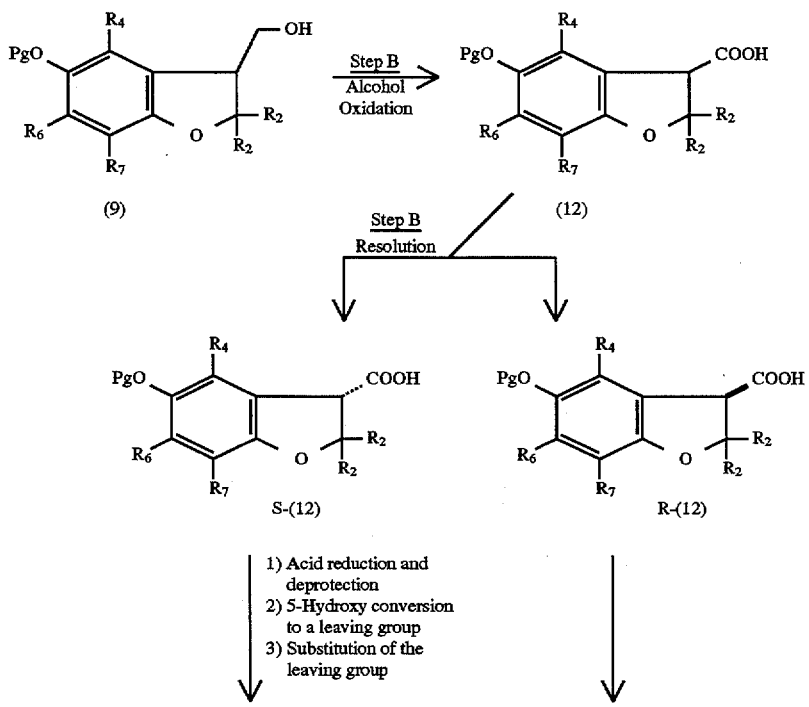

-continued
SCHEME IV

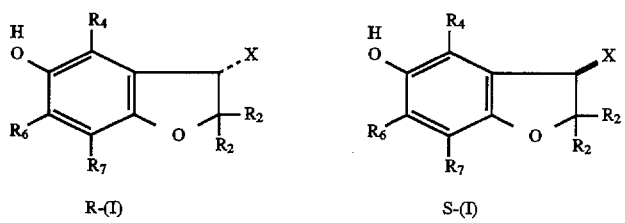

R-(I)            S-(I)

More preferably, 3-hydroxy moiety of the 3-hydroxymethyl-5-protected hydroxy-2,3-dihydro-benzofuran (9) is oxidized to aldehyde using Swern oxidation conditions as disclosed by A. J. Mancuso and D. Swern in *Synthesis*, p165, 1981 which is incorporated by reference. A Swern oxidation comprises using for example oxalyl chloride, dimethylsulfoxide and a base such as triethylamine as reagents. The reaction may be carried out in solvent such as dichloromethane at a range of temperature between −78° C. to 0° C.

The aldehyde is further oxidized to the carboxylic acid. Oxidation of the aldehyde to the carboxylic acid is well known in the art as disclosed in *Selection of Oxidantas in Synthesis* (p7–11, Chinn, Marcel Dekker, New York, 1971), which is here incorporated by reference. The aldehyde is oxidized by using for example permanganate in acidic, basic or neutral condition, chromic acid, bromine, silver oxide.

More preferably, the aldehyde is oxidized using sodium chlorite and sodium dihydrogenophosphonate as disclosed by B. S. Bal, W. E. Childers and H. W. Pinnick in *Tetrahedron*, 1981, 37, 2091, which is here incorporated by reference. The reaction is performed in alcoholic solvent such as tert-butanol, acetonitrile in presence of 2-methyl-2-butene at a range of temperature from 0° to 25° C. Thereby protected 5-hydroxy-2,3-dihydro-benzofuran-3-carboxylic acid (12) is obtained.

Alternatively, the protected 5-hydroxy-2,3-dihydrobenzofuran-3-carboxylic acid (12) may be obtained from the the benzofuranone (7) by using the following steps: Reduction of the ketone into its corresponding alcohol, transformation of this 3-hydroxy group into a leaving group, substitution of the leaving group by a cyano group which is then hydrolyzed to produce the corresponding protected 5-hydroxy-2,3-dihydro-benzofuran-3-carboxylic acid (12).

Optionally, the racemate (12) may be resolved or isolated according to conventional and standard procedures well known in the art, e.g., chromatographic separation, fractional crystallization, use of optically active esters or of optically active base, enzymatic resolution and the like.

More preferably the acid (12) is resolved by chemical resolution. For the chemical resolution the 5-hydroxy group is preferably protected by an ester group such as an acetate group this may need a previous deprotection if the 5-hydrox group is protected by an alkyl group such as a methyl or benzyl.

The deprotection of the hydroxy group protected as a methoxy is performed using common reagents of deprotection, which are for example trimethyl silyliodide, boron tribromide, boron trifluoride, trimethylsilyl methylsulfide or trimethylsilyl phenylsulfide, aluminium halide (halide being chloride or bromide), according to procedures well known in the art.

The deprotection of hydroxy group protected as a benzyloxy is commonly performed by catalytic or chemical reduction, using for example palladium on carbon in ethanol, sodium in amonia or ethanol, trimethyl silyliodide in dichloromethane, and others.

The 5-hydroxy group is then protected by an ester such as an acetate. The reaction is performed using acetic anhydride or acetyl chloride. More preferably, the most common method for acetate introduction is using acetic anhydride in pyridine at a temperature from 0° C. to 25° C. The 5-hydroxy protected compound (12) is obtained and purified by standard methods in the art.

More preferably, the enantiomers of 5-acetoxy-2,3-dihydro-benzofuran-3-carboxylic acid (12) are resolved using optically active bases. Natural and synthetic optically active bases may be used such as for example morphine, ephedrine, brucine, strychnine but also some others such as (α)-methylbenzylamine. The optically active base forms a salt with the carboxylic acid. For example if the base used has a (S) configuration there will be a mixture of two salts produced having the configurations (SS) and (SR). Although the acids are enantiomers, the salts are diastereoisomers and have different properties. The property most often used for separation is differential solubility. The mixture of diastereomeric salts is allowed to crystallize from suitable solvent. The diastereoisomers are obtained using fractional crystallization. Once the two diastereoisomers have been separated they can be easily converted into their free acids.

More preferably, 5-acetoxy-2,3-dihydro-benzofuran-3-carboxylic acid (12) is resolved using S(−)-(α)-methylbenzylamine in a mixture of solvents such as alcohols (methanol, ethanol, isopropanol), ethers (diethylether, tetrahydrofuran), ethyl acetate. More preferably a mixture of isopropanol and ethyl acetate is used. The first diastereomeric salt is obtained as crystals which can be isolated easily by filtration from the other diasteroisomer. The liltrate is then treated by acidic condition such as hydrochloric acid to recover the free acid of the second enantiomer. The free acid is extracted by organic solvent such as ethyl acetate. The second enantiomer is obtained by crystallization using R(+)-(α)-methylbenzylamine. As described previously the second enantiomer is recovered by treating the salts in acidic conditions. This resolution leads to the two enantiomers R-5-acetoxy-2,3-dihydro-benzofuran-3-carboxylic acid R-(12) and S-5-acetoxy-2,3-dihydro-benzofuran-3-carboxylic acid S-(2).

Each so-produced carboxylic acid may be reduced to their corresponding primary alcohol. They are easily reduced using lithium aluminium hydride or other hydride reagents such as sodium boron hydride, or borane complexes such as with dimethyl sulfide, tetrahydrofuran. More preferably, borane dimethyl sulfide is used in tetrahydrofuran under reflux.

Each optically active compound is then treated as previously described for the racemate to obtain each optically active 2,3-dihydro-benzofuranol derivatives (I) derived from respectively the R-5-Acetoxy-2,3-dihydrobenzofuran-3-carboxylic acid and the S-5-Acetoxy-2,3-dihydro-benzofuran-3-carboxylic acid derivatives.

Optionally, the acid (12) may be esterified to obtain compounds of formula (I) wherein X is COOR$_7$. Esterification may be conducted using well known procedures in the art as disclosed for example in "Advanced Organic Chemistry" Jerry March, John Wiley & Sons, New York, 0–24, p348–353, 1989, or in Patent Application WO93/20057, filed Mar. 10, 1993, which are incorporated herein by reference.

Optionally, the acid (12) may be transformed into an amide of formula (I) wherein X is C(O)A (A being as defined above). The formation of the amide may be carried out using well known procedures in the art as disclosed for example in "Advanced Organic ChemistrX" Jerry March, John Wiley & Sons, New York, 0–24, p371–373, 1989, or in Patent Application WO 93/20057, filed Mar. 10, 1993 and U.S. counterpart U.S. Ser. No. 08/318,633, filed Dec. 22, 1994, which are herein incorporated by reference. Optionally, the 5-hydroxy of compounds of formula (I) may be esterified using methods as mentioned above.

The process of the invention is preferred for the synthesis of compounds of formula (I)

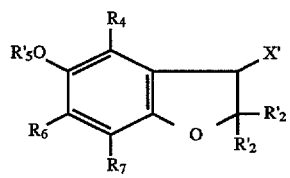

wherein:

R'$_2$ is C$_{1-4}$ alkyl each R$_2$ moiety being independently C$_{1-14}$ alkyl;

R$_4$ is C$_{1-6}$ alkyl;

R'$_5$ is H;

R$_6$ is C$_{1-6}$ alkyl;

R$_7$ is H or C$_{1-6}$ alkyl;

X' is CH$_2$A', A' is

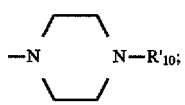

and

R'$_{10}$ is H or C$_{1-3}$ alkyl.

As for example, the preferred synthesis for the racemate and for the optically active 2,2,4,6,7-Pentamethyl-3-[(4-methylpiperazino)-methyl]-2,3-dihydro-1-benzofuran-5-ol derivatives are described respectively in the following SCHEME V, SCHEME VI and SCHEME VII. The following compounds are numbered to correspond to analogous compounds in previous claims with either V, VI or VII added to indicate the scheme.

SCHEME V:
Synthesis of the racemic 2,2,4,6,7-pentamethyl-3-[(4-methylpiperazino)-methyl]-2,3-dihydro-1-benzofuran-5-ol

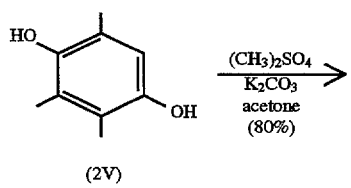

(2V)

-continued
SCHEME V:
Synthesis of the racemic 2,2,4,6,7-pentamethyl-3-[(4-methylpiperazino)-methyl]-2,3-dihydro-1-benzofuran-5-ol

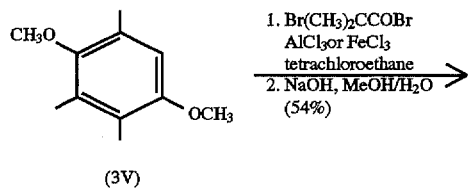

(3V)

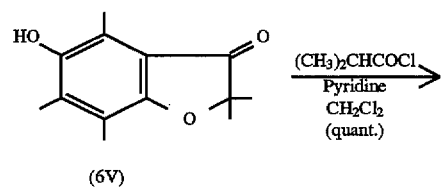

(6V)

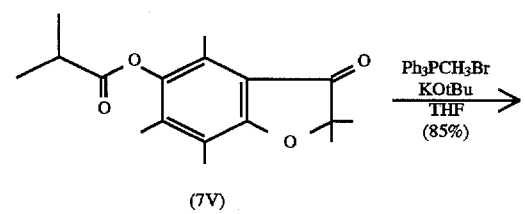

(7V)

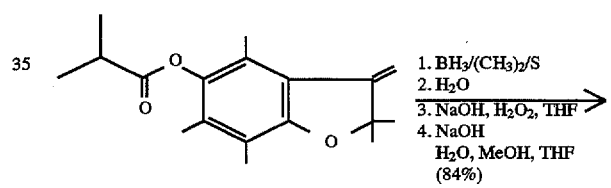

(8V)

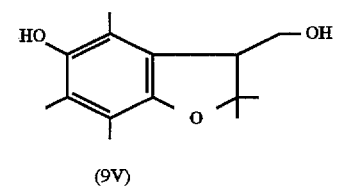

(9V)

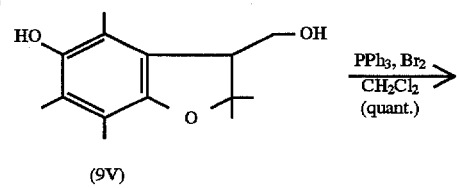

(9V)

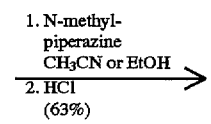

(Deprotected 10V)

SCHEME V:
Synthesis of the racemic 2,2,4,6,7-pentamethyl-3-[(4-methylpiperazino)-methyl]-2,3-dihydro-1-benzofuran-5-ol
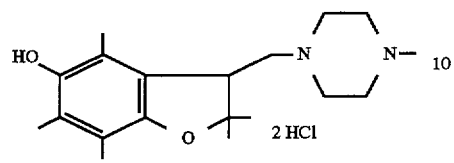
(I)-V
SCHEME VI:
Synthesis of optically active 2,2,4,6,7-pentamethyl-3-[(4-methylpiperazino)-methyl]-2,3-dihydro-1-benzofuran-5-ol by chemical resolution of the acid
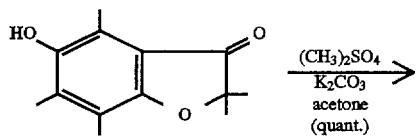
(6VI)
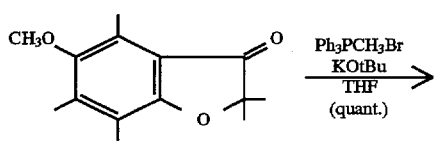
(7VI)
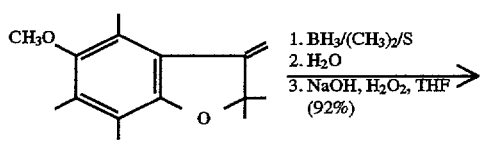
(8VI)
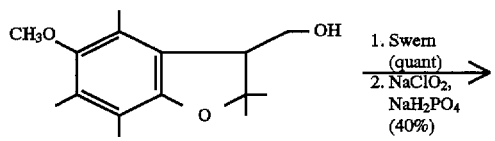
(9VI)
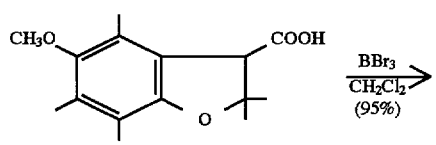
(12VI)

-continued
SCHEME VI:
Synthesis of optically active 2,2,4,6,7-pentamethyl-3-[(4-methylpiperazino)-methyl]-2,3-dihydro-1-benzofuran-5-ol by chemical resolution of the acid
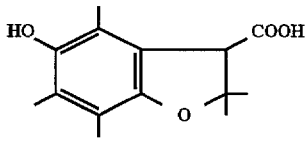
(Deprotected 12VI)
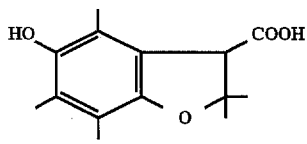
(Deprotected 12VI)
1. Ac₂O, Pyridine (81%)
2. RESOLUTION (α)-methyl-benzylamine (73%/56%)
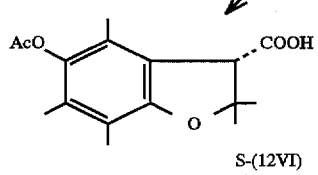
S-(12VI)
1) BH₃/(CH₃)₂S
2) PPh₃, Br₂
3) N-methyl piperazine
4) HCl
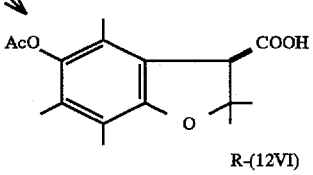
R-(12VI)
1) BH₃/(CH₃)₂S
2) PPh₃, Br₂
3) N-methyl piperazine
4) HCl
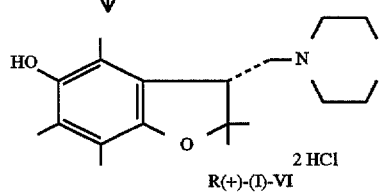
2 HCl
R(+)-(I)-VI
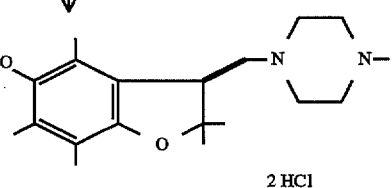
2 HCl
S(-)-(I)-VI

SCHEME VII:
Synthesis of optically active 2,2,4,6,7-pentamethyl-3-[(4-methylpiperazino)-methyl]-2,3-dihydro-1-benzofuran-5-ol using alcohol resolution

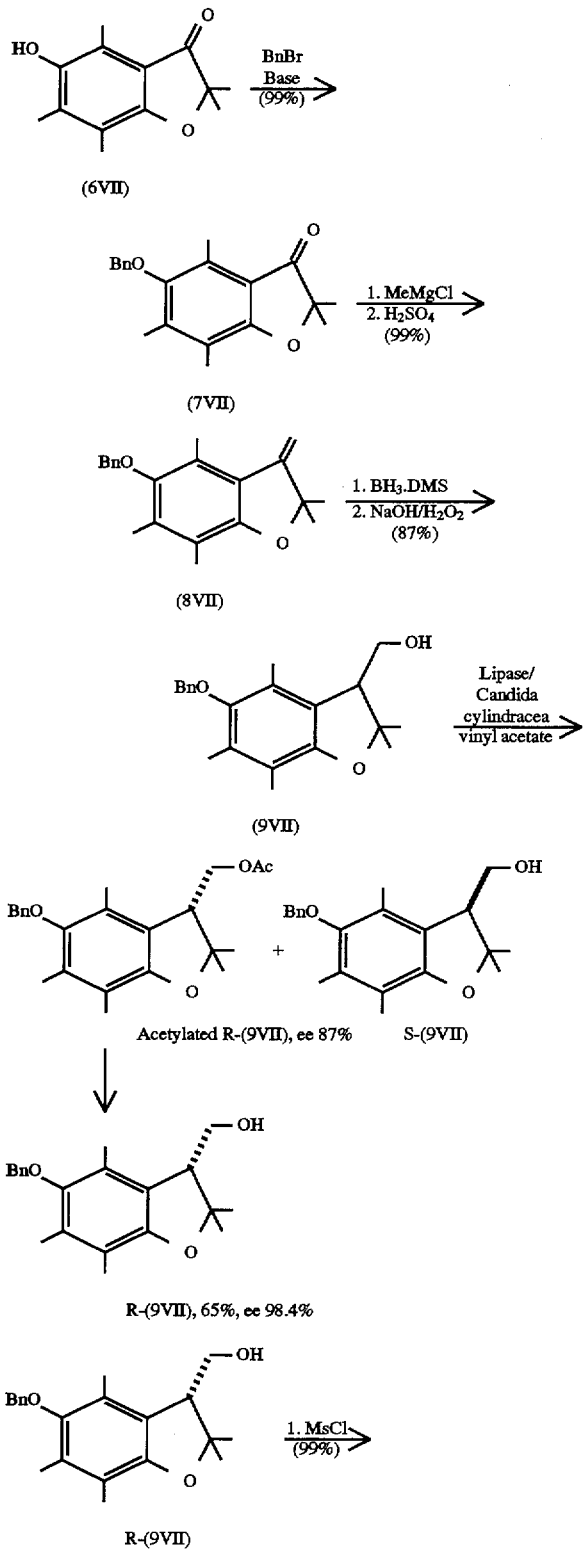

The following examples present typical syntheses as described in Scheme V, VI and Scheme VII. These examples are understood to be illustrative only and are not intended to limit the scope of the present invention in any way. As used herein, the following terms have the indicated meanings: "g" refers to grams; "mmol" refers to millimoles; "mL" refers to millimeters; "bp" refers to boiling point; "mp" refers to melting point; "°C." refers to degrees Celsius; "mm Hg" refers to millimeters of mercury; "Pa" refers to pascals; "µt" refers to microliters; "µg" refers to micrograms; "µM" refers to micromolar; "TLC" refers to thin layer chromatography; "M" refers to mo! arity; "N" refers to normal; "[α]$_D^{20}$" refers to specific rotation of the D line of sodium at 20° C. obtained in a 1 decimeter cell; "GC" refers to gas chromatography; and "Rf" refers to retention factor.

EXAMPLE 1

1,4-DIMETHOXY-2,3,5-TRIMETHYLHYDROQUINONE (3 V)

A mixture of trimethylhydroquinone (60.87 g, 0.4 mol), dimethylsulfate (151.36 g, 1.2 mol) and potassium carbonate (221 g, 1.6 mol) in acetone (1.6 L) is refluxed for three days under nitrogen. After cooling, 10% sodium hydroxide (400 mL) is added and most of the acetone is evaporated. The black mixture is taken up in heptane (800 mL), the organic phase is separated and washed with 10% sodium hydroxide (2×200 mL), water (200 mL) and brine (200 mL). The solvent is dried (magnesium sulfate) and evaporated under reduced pressure to give a yellow oil. Purification on a small pad of silica gel eluting with heptane/ethyl acetate 95:5 gave 57.4 g (80%) of 1,4-dimethoxy-2,3,5-trimethylhydroquinone as a colorless oil which slowly crystallized.

To avoid the formation of large amount of 2,3,5-trimethyl-1,4-benzoquinone, nitrogen is previously bubbled for 30 min into acetone. Compound 1,4-dimethoxy-2,3,5-trimethylhydroquinone may be purified by distillation.

EXAMPLE 2

5-HYDROXY-2,2,4,6,7-PENTAMETHYL-2,3-DIYDRO-1-BENZOFURAN-3-ONE

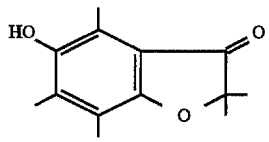
(6 V)

Aluminium chloride (25 g, 188 mmol) is added portionwise at 0° C. and under nitrogen to a solution of 1,4-dimethoxy-2,3,5-trimethyihydroquinone (33.83 g, 188 mmol) and 2-bromo-2-methylpropionylbromide (129.46 g, 563 mmol) in tetrachloroethane (188 mL). The dark solution is then heated at 70° C. until completion of the reaction (3–5 days) as indicated by TLC (heptane/ethyl acetate 90:10). The reaction is quenched by careful addition of ice. The black mixture is acidified to pH 1 with concentrated hydrochloric acid and extracted with dichloromethane (2×150 mL). The organic phase is washed with water (150 mL), 10% potassium bicarbonate (2×150 mL), dried (magnesium sulfate) and evaporated to dryness. The residue (106 g) is triturated in heptane in the aim to precipitate the 1,4-di-(2-bromo-2-methylpropionoxy)-2,3,5-trimethylhydroquinone formed during the reaction and filtered off (30.15 g). The filtrate is evaporated to dryness and the residue (66.37 g) is passed through a small pad of silica gel eluting with heptane/ethyl acetate 95:5 to give 39.78 g of crude 5-(2-bromo-2-methylpropionoxy)-2,2,4,6,7-pentamethyl-2,3-dihydro-1-benzofuran-3-one (Rf=0.4 heptane/ethyl acetate 90:10). The yellow solid is dissolved in a mixture of methanol/tetrahydrofuran (400 mL, 1:1) and sodium hydroxide (20 g, 500 mmol) in water (100 mL) is added dropwise under nitrogen. The solution is stirred for 4 hrs at 60° C. and overnight at room temperature. The black mixture is then acidified with concentrated hydrochloric acid. Most of the solvent is evaporated under reduced pressure and the residue is taken up in ethyl acetate (300 mL). The organic phase is washed with water (150 mL), 10% sodium bicarbonate (2×150 mL), brine, dried (magnesium sulfate) and evaporated to dryness to give 22.39 g of the crude 5-hydroxy-2, 2,4,6,7-pentamethyl-2,3-dihydro-1-benzofuran-3-one as a yellow powder. A sample is recrystallized in heptane/diisopropyloxide, mp=142° C.–144° C. Rf=0.29 (heptane/ethyl acetate 80:20)

EXAMPLE 3

5-(2-METHYLPROPIONOXY)-2,2,4,6,7-PENTAMETHYL-2,3-DIHYDRO-1-BENZOFURAN-3-ONE

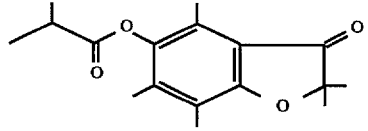
(7 V)

A solution of 2-methylpropionylchloride (isobutyrylchloride, 8.05 g, 75.55 mmol) in dichloromethane (10 mL) is added dropwise at 0° C. and under nitrogen to a solution of 5-hydroxy-2,2,4,6,7-pentamethyl-2,3-dihydro-1-benzofuran-3-one (12.8 g, 58.11 mmol) and pyridine (5.97 g, 61 mmol) in dichloromethane (58 mL). The ice bath is removed and the mixture is stirred for 2 hrs at room temperature. Water (10 mL) is added and the organic phase is washed with 2N hydrochloric acid (100 mL), water (100 mL), 10% sodium bicarbonate (100 mL) and brine. The solution is dried (magnesium sulfate) and evaporated to dryness to give 17 g (100%) of 5-(2-methylpropionoxy)-2, 2,4,6,7-pentamethyl-2,3-dihydro-1-benzofuran-3-one as an oil which is used without purification for the next step. Rf=0.5 (heptane/ethyl acetate 90:10)

EXAMPLE 4

3-METHYLENE-5-(2-METHYLPROPIONOXY)-2, 2,4,6,7-PENTAMETHYL-2,3-DIHYDRO-1-BENZOFURAN

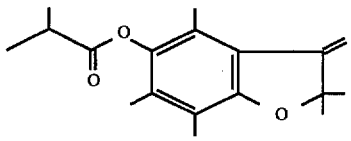
(8 V)

Potassium tert-butoxide (1.53 g, 13.68 mmol) is added portionwise at 0° C. and under nitrogen to a suspension of methyltriphenylphosphonium bromide (4.9 g, 13.68 mmol) in dry tetrahydrofuran (57 mL) and the reaction mixture is stirred for 1 hr at room temperature. The 5-(2-methylpropionoxy)-2,2,4,6,7-pentamethyl-2,3-dihydro-1-benzofuran-3-one (3.31 g, 11.4 mmol) in dry tetrahydrofuran (20 mL) is dropwise added at 0° C. to the yellow suspension and the reaction is stirred overnight at room temperature. Water is added and most of tetrahydrofuran is evaporated under reduced pressure. The residue is taken up in ethyl acetate, washed with brine, dried (magnesium sulfate) and the solvent is evaporated to dryness. Purification by flash chromatography eluting with heptane/ethyl acetate 95:5 and then 90:10 gave 2.8 g (85%) of 3-methylene-5-(2-methylpropionoxy)-2,2,4,6,7-pentamethyl-2,3-dihydro-1-benzofuran as a yellow oil. Rf=0.79 (heptane/ethyl acetate 70:30)

EXAMPLE 5

5-HYDROXY-3-HYDROXYMETHYL-2,2,4,6,7-PENTAMETHYL-2,3-DIHYDRO-1-BENZOFURAN

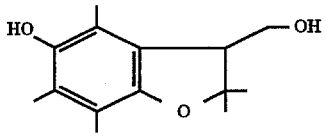
(9 V)

10M borane dimethylsulfide complex (6.1 mL, 61 mmol) is added dropwise at 0° C. and under nitrogen to a solution of 3-methylene-5-(2-methylpropionoxy)-2,2,4,6,7-pentamethyl-2,3-dihydro-1-benzofuran (11.7 g, 40.57 mmol) in tetra-hydrofuran (40 mL) and the solution is stirred at room temperature for 3 hrs. Water (10 mL) is carefully added followed by addition of 3N Sodium hydroxide (30 mL) and 30% hydrogen peroxide (10.1 mL). After stirring 2 hrs at room temperature, most of tetrahydrofuran is evaporated and the residue is extracted with ethyl acetate. The organic phase is washed with 10% sodium sulfite (10 mL), water (100 mL), brine dried (magnesium sulfate) and evaporated to dryness to give 13.29 g of a mixture of 5-hydroxy-3-hydroxymethyl-2,2,4,6,7-pentamethyl-2,3-dihydro-1-benzofuran (Rf=0.37 heptane/ethyl acetate 50:50) and of the corresponding 5-isobutyryl ester (Rf=0.57 heptane/ethyl acetate 50:50). The residue is then treated for 2 hrs at 80° C. with Sodium hydroxide (6.5 g, 162 mmol) in a mixture of water/methanol/tetrahydrofuran 40:20:20. In hydrochloric acid is added until pH 1 and most of the solvent is removed under reduced pressure. The residue is taken up in ethyl acetate and the organic phase is washed with water, brine, dried (magnesium sulfate) and evaporated to dryness. Purification by flash chromatography eluting with heptane/ethyl acetate 80:20 to 50:50 gave 8.05 g (84%) of 5-hydroxy-3-hydroxymethyl-2,2,4,6,7-pentamethyl-2,3-dihydro-1-benzofuran as a yellow oil which slowly crystallized. A sample is recrystallized from ethyl acetate/heptane, mp=89°–90° C.

EXAMPLE 6

3-BROMOMETHYL-2,2,4,6,7-PENTAMETHYL-2,3-DIHYDRO-1-BENZOFURAN-5-OL

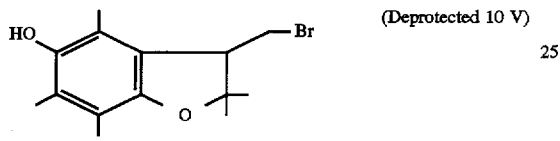

(Deprotected 10 V)

To an ice-cooled solution of triphenylphosphine (41.89 g, 160 mmol) in dichloromethane (120 mL) is added dropwise a solution of bromine (24.33 g, 152 mmol) in dichloromethane (40 mL) and the resulting mixture is stirred at 0° C. for 1 hr giving a white precipitate free of bromine coloration. To this mixture is added alcohol 5-hydroxy-3-hydroxymethyl-2,2,4,6,7-pentamethyl-2,3-dihydro-1-benzofuran (34.26 g, 145 mmol) and the resulting solution is allowed to warm to room temperature and stirred for 18 hrs. The solution is concentrated to a small volume and is chromatographed on silica gel using dichloromethane/hexane 1:2 as eluent. Fractions containing the product are combined and evaporated to give 43.28 g (99%) of 3-bromomethyl-2,2,4,6,7-pentamethyl-2,3-dihydro-1-benzofuran-5-ol as an oil. A sample is recrystallized from ethyl acetate/heptane, mp 79° C.–80° C.

EXAMPLE 7

2,2,4,6,7-PENTAMETHYL-3-[(4-METHYLPIPERAZINO)-METHYL]-2,3-DIHYDRO-1-BENZOFURAN-5-OL DIHYDROCHLORIDE HYDRATE

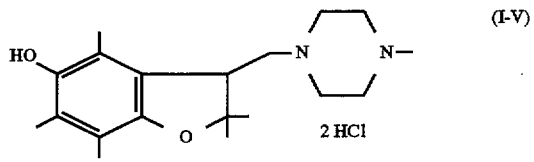

(I-V)

A solution of 3-bromomethyl-2,2,4,6,7-pentamethyl-2,3-dihydro-1-benzofuran-5-ol (81 g, 270 mmol), phenol (26.75 g, 284 mmol) and N-methylpiperazine (28.47 g, 284 mmol) in acetonitrile (300 ml) is stirred at reflux temperature for 60 hrs. The precipitate that formed is collected, washed with acetonitrile and slurried in 10% sodium bicarbonate solution. The product is extracted twice with ethyl acetate, and the extract is washed with water and brine, dried (sodium sulfate) and evaporated. The resulting solid is dissolved in ethanol (150 mL) and 2N hydrochloric acid (150 mL), and evaporated to near dryness. The resulting solid is recrystallized in ethanol/ethyl acetate to give after drying at 60° C. under 13 Pa and equilibration in a moist atmosphere for 24 hrs, 48.60 g (44%) of 2,2,4,6,7-pentamethyl-3-[(4-methylpiperazino)-methyl]-2,3-dihydro-1-benzofuran-5-ol dihydrochloride hydrate, mp=172°–3° C.(dec.). A second crop of 19.63 g of 2,2,4,6,7-pentamethyl-3-[(4-methylpiperazino)-methyl]-2,3-dihydro-1-benzofuran-5-ol (total yield 63%) could be obtained from the filtrate after purification of the free base by column chromatography on silica gel eluting with dichloromethane/methanol 9:1.

EXAMPLE 8

5-METHOXY-2,2,4,6,7-PENTAMETHYL-2,3-DIHYDRO-1-BENZOFURAN-3-ONE

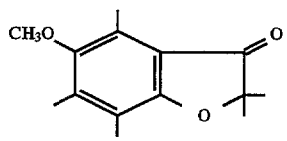

(7 VI)

A mixture of phenol 5-hydroxy-2,2,4,6,7-pentamethyl-2,3-dihydro-1-benzofuran-3-one (7.16 g, 32.54 mmol), dimethylsulfate (6.16 g, 48.8 mmol) and potassium carbonate (13.5 g, 97.63 mmol) in acetone (160 mL) is refluxed under nitrogen for 3 days. After cooling, 3N sodium hydroxide (100 mL) is added and most of the acetone is evaporated under reduced pressure. The mixture is extracted with ethyl acetate (200 mL) and the organic layer is washed with 3N sodium hydroxide (2×100 mL), water, brine, dried (magnesium sulfate)and evaporated to dryness to give 7.52 g (99%) of 5-methoxy-2,2,4,6,7-pentamethyl-2,3-dihydro-1-benzofuran-3-one as a yellow solid which is used without purification for the next step. Rf=0.4 (heptane/ethyl acetate 90:10)

EXAMPLE 9

5-METHOXY-3-METHYLENE-2,2,4,6,7-PENTAMETHYL-2,3-DIHYDRO-1-BENZOFURAN

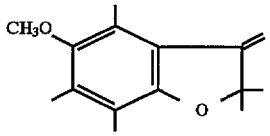

(8 VI)

Potassium tert-butoxide (4 g, 35.5 mmol) is added portionwise at 0° C. and under nitrogen to a suspension of methyltriphenylphosphonium bromide (12.7 g, 35.5 mmol) in dry tetrahydrofuran (120 mL) and the reaction mixture is stirred for 1 hr at room temperature. The 5-methoxy-2,2,4,6,7-pentamethyl-2,3-dihydro-1-benzofuran-3-one (5.55 g, 23.7 mmol) in dry tetrahydrofuran (40 mL) is added dropwise at 0° C. to the yellow suspension and the reaction is stirred overnight at room temperature. Water (50 mL) is carefully added and most of the solvent is evaporated under reduced pressure. The residue is taken in ethyl acetate (200 mL), washed with brine, dried (magnesium sulfate) and evaporated to dryness. Purification through a small pad of silica gel using dichloromethane as a solvent gave 5.47 g 5-methoxy-3-methylene-2,2,4,6,7-pentamethyl-2,3-dihydro-1-benzofuran (99%) as a yellow oil. Rf=0.48 (heptane/ethyl acetate 90:10).

EXAMPLE 10

3-HYDROXYMETHYL-5-METHOXY-2,2,4,6,7-PENTAMETHYL-2,3-DIHYDRO-1-BENZOFURAN

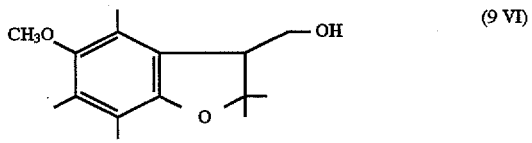

(9 VI)

10M borane dimethylsulfide complex (2.08 mL, 20.8 mmol) is added dropwise at 0° C. and under nitrogen to a solution of 5-methoxy-3-methylene-2,2,4,6,7-pentamethyl-2,3-dihydro-1-benzofuran (4.03 g, 17.35 mmol) in dry tetrahydrofuran (35 mL). The solution is stirred at room temperature for 2 hrs. Water (10 mL) is carefully added to the solution at 0° C., followed by addition of 3N sodium hydroxide (5.78 mL) and hydrogen peroxide (5.78 mL). After 2 hrs. at room temperature, most of the tetrahydrofuran is evaporated to dryness and the residue is extracted with ethyl acetate (2×100 mL). The combined organic phases are washed with 10% sodium sulfite, water, brine, dried (magnesium sulfate) and evaporated to dryness to give 4.2 g of crude alcohol. Purification by flash chromatography eluting with heptane/ethyl acetate 70:30 and then 60:40 gave 4 g (92%) 3-hydroxymethyl-5-methoxy-2,2,4,6,7-pentamethyl-2,3-dihydro-1-benzofuran of as a white powder. A sample is recrystallized from hexane, mp=79°–81° C. Rf=0.28 (heptane/ethyl acetate 70:30).

EXAMPLE 11

5-METHOXY-2,2,4,6,7-PENTAMETHYL-2,3-DIHYDRO-1-BENZOFUR, AN-3-CARBOXYLIC ACID a) Swern Oxidation

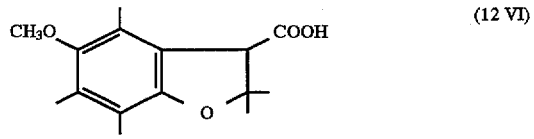

(12 VI)

Dimethylsulfoxide (687 mg, 8.8 mmol) in dichloromethane (10 mL) is added dropwise at −60° C. and under nitrogen to a solution of oxalyl chloride (558 mg, 4.4 mmol) in dichloromethane (20 mL). The reaction is stirred for 5 min and the 3-hydroxymethyl-5-methoxy-2,2,4,6,7-pentamethyl-2,3-dihydro-1-benzofuran (1g, 4 mmol) in dichloromethane (10 mL) is added dropwise. After 15 min stirring, triethylamine (2.02 g, 30 mmol) is added dropwise to the solution. The cooled bath is removed and the solution is stirred at room temperature for 2 hrs. Water (40 mL) is added. The organic phase is dried (magnesium sulfate) and evaporated to dryness to give crude aldehyde (1 g, 100%) which is used without purification for the next step.
b) Oxidation of the aldehyde to the carboxylic acid 5-methoxy-2,2,4,6,7-pentamethyl-2,3-dihydro-1-benzofuran-3-carboxylic acid.

The procedure described by B. S. Bal, W. E. Childers and H. W. Pinnick in Tetrahedron 1981, 37 2091 is followed with minor modifications. The crude aldehyde (1 g, 4 mmol) is dissolved in tert-butanol (83 mL) and 2-methyl-2-butene (13.22 g, 188.5 mmol). A solution of sodium chlorite (3.31 g, 36.6 mmol) and sodium dihydrogenophosphate monohydrate (3.81 g, 27.64 mmol) in water (33 mL) is added dropwise over a 10 min period. The pale yellow reaction mixture is stirred at room temperature for 1 hr. Volatile components are then removed under vacuum, the residue is taken up in ether (30 mL) and extracted with 10% potassium carbonate (3×30 mL). The combined aqueous phases are acidified with concentrated hydrochloric acid and extracted with ethyl acetate (2×30 mL). The organic phases are washed with brine, dried (magnesium sulfate) and evaporated to dryness to give 440 mg (41%) of 5-methoxy-2,2,4,6,7-pentamethyl-2,3-dihydro-1-benzofuran-3-carboxylic acid as a white solid.

A sample is recrystallized in heptane/ethyl acetate, mp=185° C.–187° C.

EXAMPLE 12

5-HYDROXY-2,2,4,6,7-PENTAMETHYL-2,3-DIHYDRO-1-BENZOFURAN-3-CARBOXYLIC ACID

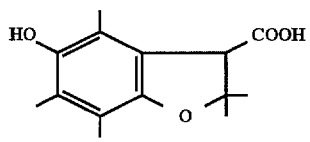

(Deprotected 12 VI)

Boron tribromide (0.42 mL of 1M solution in dichloromethane, 0.42 mmol) is added dropwise at −78° C. and under nitrogen to a solution of 5-methoxy-2,2,4,6,7-pentamethyl-2,3-dihydro-1-benzofuran-3-carboxylic acid (100 mg, 0.38 mmol) in dichloromethane (4 mL). The reaction mixture is allowed to warm to room temperature and stirred overnight. The reaction is quenched by addition of water (10 mL) and extracted with dichloromethane (2×20 mL). The organic phase is dried (magnesium sulfate) and evaporated to dryness to give 90 mg (95%) of 5-hydroxy-2,2,4,6,7-pentamethyl-2,3-dihydro-1-benzofuran-3-carboxylic acid as a white solid. A sample is recrystallized in heptane/ethyl acetate, mp=182°–184° C.

EXAMPLE 13

5-Acetoxy -2,2,4,6,7-pentamethyl-2,3-dihydro-1-benzofuran-3-carboxylic acid

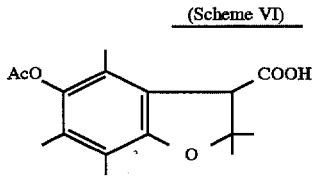

(Scheme VI)

To a solution of 5-hydroxy-2,2,4,6,7-pentamethyl-2,3-dihydro-1-benzofuran-3-carboxylic acid (25.03 g, 100 mmol) in pyridine (200 mL) is added acetic anhydride (100 mL) and the mixture is stirred at room temperature for 24 hrs. Water and ice are added and the mixture is stirred at about 30° C. for 30 min. The mixture is cooled in ice and 6N hydrochloric acid (450 mL) is added. The resulting solid is collected, washed with water, taken up in ethyl acetate. The organic layer is washed with 2N hydrochloric acid and water, dried (sodium sulfate) and evaporated to dryness. Recrystallization from ethyl acetate gave 23.6 g (81%) of 5-acetoxy-2,2,4,6,7-pentamethyl-2,3-dihydro-1-benzofuran-3-carboxylic acid (mp=187° C.–188° C.).

EXAMPLE 14

CHEMICAL RESOLUTION OF THE CARBOCYCLIC ACID DERIVATIVE OF EXAMPLE 13

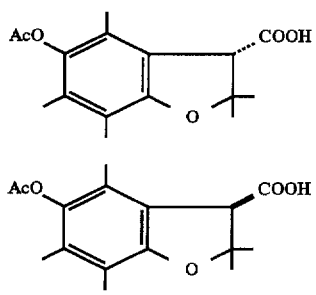

S-(12 VI)

R-(12 VI)

A solution of 5-Acetoxy-2,2,4,6,7-pentamethyl-2,3-dihydro-1-benzofuran-3-carboxylic acid (15.27 g, 52.3 mmol) and S(–)-α-methylbenzylamine (6.65 g, 54.9 mmol) in a mixture of isopropanol (100 mL), water (2 mL) and ethyl acetate (300 mL) is evaporated to a volume of about 100 mL. The crystalline material obtained after standing at room temperature is recrystallized twice from the same solvent mixture to give 6.02 g (56%) of the diastereomeric salt $[\alpha]_D^{25}$=–13.81 (0.99 in methanol), ee=99.9%. The combined filtrates are suspended in water and 2N hydrochloric acid (50 mL) is added. The mixture is extracted twice with ethyl acetate. The extract is washed with 2N hydrochloric acid, brine, dried (Sodium sulfate) and evaporated to give 11.34 g of an oil. To this is added R(+)-α-methylbenzylamine (4.7 g, 38.8 mmol) and crystallization is obtained using the same solvent mixture described above. Two recrystallizations gave 7.9 g (73%) of the other diastereomeric salt, $[\alpha]_D^{25}$=–14.21 (0.99 in methanol) ee=99.9%.

Each diastereoisomeric salt is converted to its free acid reduced to the corresponding alcohol 3-hydroxymethyl-5-methoxy-2,2,4,6,7-pentamethyl-2,3-dihydro-1-benzofuran with borane-dimethylsulfate complex, converted to 3-bromomethyl-2,2,4,6,7-pentamethyl-2,3-dihydro-1-benzofuran-5-ol with triphenylphosphine/bromine and reacted with N-methylpiperazine under the same conditions as described previously.

R(+)-(2,2,4,6,7-PENTAMETHYL-3-[(4-METHYLPIPERAZINO)-METHYL]-2,3-DIHYDRO-1-BENZOFURAN-5-OL) is obtained from the diastereomeric salt of 5-acetoxy-2,2,4,6,7-pentamethyl-2,3-dihydro-1-benzofuran-3-carboxylic acid with R(+)-α-methylbenzylamine, mp 265° C. (decomposition), $[\alpha]_D^{20}$= +20.68 (1.18 in water, pH=1.4). Weight loss on heating (40° C./min, 40° C. to 175° C.) 4.22%=1.02 mmol of water.

S(–)-(2,2,4,6,7-PENTAMETHYL-3-[(4-METHYLPIPERAZINO)-METHYL]-2,3-DIHYDRO-1-BENZOFURAN-5-OL) is obtained from the diastereomeric salt of 5-acetoxy-2,2,4,6,7-pentamethyl-2,3-dihydro-1-benzofuran-3-carboxylic acid with S(–)-α-methylbenzylamine, mp 267° C. (decomposition), $[\alpha]_D^{20}$= –20.66 (1.66 in water, pH=1). Weight loss on heating (40° C./min, 40° C. to 175° C.) 3.95%=0.97 mmol of water.

X-ray crystallography showed the salt with R-(+)-amine to have the S configuration. Due to the nomenclature conventions, the enantiomer of derived from the S-acid, has the R configuration.

EXAMPLE 15

5-BENZYLOXY-2,2,4,6,7-PENTAMETHYL-2,3-DIHYDRO-1-BENZOFURAN-3-ONE

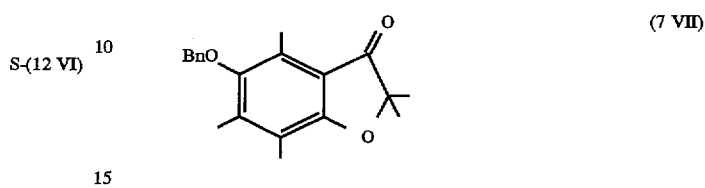

(7 VII)

Potassium carbonate (720 g) is added to a solution of 5-hydroxy-2,2,4,6,7-pentamethyl-2,3-dihydro-1-benzofuran-3-one (453 g, 2.1 mol) in acetone (2 L). A solution of benzyl bromide (423 g, 2.5 mmol) in acetone (200 mL) is added portionwise over a period of 10 min. A slight exotherm is observed. After 3 hrs, the mixture is heated to reflux. After 39 hrs, TLC shows complete conversion to product. The mixture is cooled to 50° C. and filtered using 1.5 L of ethyl acetate to remove the solids from the flask. The solids are washed with ethyl acetate (1.5 L). The filtrate is concentrated. The resulting solids are dissolved in ethyl acetate (7 L). This solution is washed with water, dried (magnesium sulfate) and concentrated. The resulting solids are placed on a tray for air-drying. After 2 days, 5-benzyloxy-2,2,4,6,7-pentamethyl-2,3-d3-onenzofuran-3-one is collected (638g, 99%). mp=114° C.–115° C.

EXAMPLE 16

5-BENZYLOXY-3-METHYLENE-2,2,4,6,7-PENTAMETHYL-2,3-DIHYDRO-1-BENZOFURAN

(8 VII)

A solution of methylmagnesium chloride 3.0M (800 mL, 2.4 mol) in tetrahydrofuran is added to a solution of 5-benzyloxy-2,2,4,6,7-pentamethyl-2,3-dihydro-1-benzofuran-3-one (500 g, 1.6 mol) in tetrahydrofuran at 0° C. over a period of one hr. The mixture is allowed to warm to room temperature. After 15 hrs, TLC and GC showed complete conversion to 5-benzyloxy-2,2,3,4,6,7-hexamethyl-2,3-dihydro-1-benzofuran-3-ol. The mixture is cooled to 0° C. and a saturated solution of ammonium chloride (350 mL) is added very carefully. Concentrated sulfuric acid (300 mL) is added dropwise over 1 hr. TLC showed conversion to 5-benzyloxy-3-methylene-2,2,4,6,7-pentamethyl-2,3-dihydro-1-benzofuran. Water (1.5 L), ethyl acetate (1.5 L), and a solution of ammonium chloride (1 L) are added to dissolve the salts. The organic phase is dried (magnesium sulfate) and concentrated. The crude oil is transferred to crystallization dish using minimal ethyl acetate and seeded. Complete crystallization is obtained in ca. 30 min. The solid is placed on a tray and allowed to air-dry. After 2 days 5-benzyloxy-3-methylene-2,2,4,6,7-pentamethyl-2,3-dihydro-1-benzofuran (492 g, 99%) is collected. mp=55°–57° C.

EXAMPLE 17

5-BENZYLOXY-3-HYDROXYMETHYL-2,2,4,6,7-PENTAMETHYL-2,3-DIHYDRO-1-BENZOFURAN

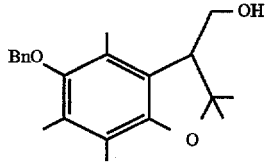

(9 VII)

A solution of complex borane-dimethyl sulfide (2.0M) in tetrahydrofuran (950 mL, 1.9 mol) is added over 2 hrs to a solution of 5-benzyloxy-3-methylene-2,2,4,6,7-pentamethyl-2,3-dihydro-1-benzofuran (492 g, 1.6 mol) in tetrahydrofuran (1.6 L) under nitrogen and cooled with an ice bath. The pot temperature is maintained between 0° C.–5° C. The solution is allowed to warm to room temperature. After 15 hrs, the solution is cooled with an ice bath and water (900 mL) is carefully added (hydrogen evolution ceased after ca. 30 mL of water has been introduced). A solution of sodium hydroxide (3.0M, 530 mL) is added over 30 min. maintaining the pot temperature below 10° C. A solution of hydrogen peroxide 30% (530 mL) is introduced keeping the pot temperature below 20° C. After 3 hrs, water (1 L), ethyl acetate (1 L) are added. Many solids formed (Note upon acidification of the aqueous waste, all of the solids dissolved easily. Perhaps acidification here might better dissolve the salts). The organic phase is separated and the aqueous phase is extracted with ethyl acetate. The combined organic phases are dried and concentrated. The oily residue is poured into hexane (1 L) using hexane (800 mL). White crystals are formed. The solids are scraped from the side and swirled to increase the crystallization. The solid is collected and air dried to give 5-benzyloxy-3-hydroxymethyl-2,2,4,6,7-pentamethyl-2,3-dihydro-1-benzofuran (371 g). The mother liquor is boiled down to 700 mL and charcoal is added. After filtering through celite, seed crystals are added. Nitrogen is blown on the solution to evaporate the hexane. The oil is washed off the solid using hexane. The solid is collected and washed thoroughly with hexane to provide 5-benzyloxy-3-hydroxymethyl-2,2,4,6,7-pentamethyl-2,3-dihydro-1-benzofuran (28 g). The mother liquor is concentrated. The resulting oil is plug filtered using 1.8 L of gravity silica gel collecting 4 (500 mL) fractions of 100% hexane, 6 (500 mL) fractions of 5% ethyl acetate/hexane, 4 (500 mL) fractions of 10% ethyl acetate/hexane, and 4 (500 mL) fractions of 20% ethyl acetate/hexane. The fractions containing the desired product are concentrated. The oil is transferred to an erlenmeyer using hexane (300 mL). After standing overnight, 5-benzyloxy-3-hydroxymethyl-2,2,4,6,7-pentamethyl-2,3-dihydro-1-benzofuran (42 g) is collected. The mixed fractions and the mother liquor from above are concentrated and plug filtered through 1 L of gravity silica gel collecting 2 (250 mL) fractions of 100% hexane, 8 (250 mL) fractions of 5% ethyl acetate/hexane, 10 (250 mL) fractions of 10% ethyl acetate/hexane, 10 (250 mL) fractions of 20% ethyl acetate/hexane. Fractions containing the desired product are combined. The residue is dissolved in hexane (100 mL). After standing overnight, 10 g of 5-benzyloxy-3-hydroxymethyl-2,2,4,6,7-pentamethyl-2,3-dihydro-1-benzofuran are collected. Total of 5-benzyloxy-3-hydroxymethyl-2,2,4,6,7-pentamethyl-2,3-dihydro-1-benzofuran collected is (451 g, 87%).

EXAMPLE 18

R-5-BENZYLOXY-3-HYDROXYMETHYL-2,2,4,6,7-PENTAMETHYL-2,3-DIHYDRO-1-BENZOFURAN

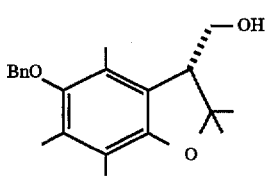

R-(9 VII)

A mixture of 5-benzyloxy-3-hydroxymethyl-2,2,4,6,7-pentamethyl-2,3-dihydro-1-benzofuran (40.1 g; 0.12 mol), lipase/*Candida cylindracea* (132 g), vinyl acetate (35.0 g; 0.41 mol) and t-butyl methyl ether (1800 mL) are combined and stirred for 24 hrs. The mixture is filtered and the filtrate is concentrated (60° C./15 tor) to constant weight. The residue is chromatographed over silica gel (hexane:ethyl acetate; 4:1) and the first fractions contained the desired acetate (19.7 g, e.e. 87%, R configuration). The so-produced acetate (19.7 g, 0.053 mol) is dissolved in 400 mL methanol and treated with potassium carbonate (2.0 g, 0.014 mol). The mixture is stirred at room temperature for 5 hrs. (TLC; no starting material present), and then the solvent is evaporated (60° C./15 tor). The residue is taken up in ether/water and the ether extract is washed with brine and dried over magnesium sulfate. The solvent is evaporated to give 17.0 g oily residue which is dissolved in 800 mL hexane. Crystallization occurred over a 48 hrs period. The solvent is decanted from the crystal mass and without disturbing the crystal mass cold hexane (150 mL) is added and gently swirled. The hexane is decanted and an additional 150 mL of cold hexane is added and the R-5-benzyloxy-3-hydroxymethyl-2,2,4,6,7-pentamethyl-2,3-dihydro-1-benzofuran is collected and dried to give 10.9 g (27%) white solid (e.e. 98.4%, $[\alpha]_D^{20}=+7.9$ in methanol).

Anal.Calc'd for $C_{21}H_{26}O_3$; C,77.27; H,8.03. Found; C, 77.35; H, 7.96.

Process for recycling the S-5-benzyloxy-3-hydroxymethyl-2,2,4,6,7-pentamethyl-2,3-dihydro-1-benzofuran.

Mesyl chloride (13.3 g, 116 mmol) is added portionwise over 30 min. to a solution of S-5-benzyloxy-3-hydroxymetkyl-2,2,4,6,7-pentamethyl-2,3-dihydro-1-benzofuran (31.6 g, 97 mol) and triethylamine (11.8 g, 116 mmol) in tetrahydrofuran (300 mL) at 0° C. The mixture is allowed to warm to room temperature. After 3 hrs, potassium tert-butoxide (39 g, 348 mmol) in tetrahydrofuran (200 mL) is added over 30 min. The solution is allowed to warm to room temperature. After 1 hr, water and ethyl acetate are added. The organic phase was washed with brine, dried (magnesium sulfate), and concentrated. The oil was transferred to a crystallization dish using minimal hexane and seeded. Complete crystallization occurred after 30 min. The solid is allowed to air dry overnight to give 30.2 g (98%) of 5-benzyloxy-3-methylene-2,2,4,6,7-pentamethyl-2,3-dihydro-1-benzofuran and recycle. Total yield of 5-benzyloxy-3-hydroxymethyl-2,2,4,6,7-pentamethyi-2,3-dihydro-1-benzofuran after 3 recycles 65%.

EXAMPLE 19

R-5-BENZYLOXY-3-(METHANESULFONATO)-2,3-DIHYDRO-2,2,4,6,7-PENTAMETHYL-1-BENZOFURAN

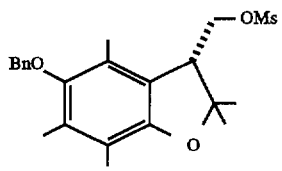

R-(10 VII)

Methanesulfonyl chloride (8.4 g, 74 mmol) is added portionwise over 15 min to a solution of R-5-benzyloxy-3-hydroxymethyl-2,2,4,6,7-pentamethyl-2,3-dihydro-1-benzofuran (20 g, 61 mmol) and triethylamine (7.5 g, 74 mmol) in tetrahydrofuran (200 mL) at 0° C. After 30 min, the mixture is allowed to warm to room temperature. After 3 hrs, the mixture (now a slurry of a white solid) is poured into 5% hydrochloric acid (200 mL) using ethyl acetate (100 mL). The organic phase is washed with brine, dried (magnesium sulfate) and concentrated to give R-5-benzyloxy-3-(methanesulfonato)-2,3-dihydro-2,2,4,6,7-pentamethyl-1-benzofuran-3-methanol as a white solid (24.7g, 99%). mp=122°–123° C., $[\alpha]_D^{20}$ (methanol)=+10.5.

EXAMPLE 20

R-5-HYDROXY-3-[(4-METHYLPIPERAZINO)-METHYL]-2,3-DIHYDRO-2,2,4,6,7-PENTAMETHYL-1-BENZOFURAN DIHYDROCHLORIDE HYDRATE

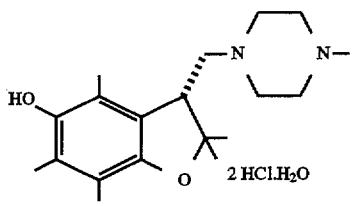

R(+)-(I-VII)

A mixture of R-5-benzyloxy-3-(methanesulfonato)-2,3-dihydro-2,2,4,6,7-pentamethyl-1-benzofuran (13.3 g, 33 mmol) and 4-methylpiperazine (6.6 g, 66 mmol), and potassium carbonate (18 g, 0.13 mol) in acetonitrile (200 mL) is heated under reflux for 18 hrs. The mixture is cooled to room temperature and concentrated. The residue is dissolved in water/chloroform. The aqueous phase is extracted with chloroform. The combined organic phases are dried (magnesium sulfate) and concentrated to give crude R-5-hydroxy-3-[(4-methylpiperazino)-methyl]-2,3-dihydro-2,2,4,6,7-pentamethyl-1-benzofuran (16 g). The crude product is dissolved in ethanol (50 mL) and acetic acid (50 mL) and added to 1.0 g of 10% palladium on carbon in a Parr bottle. This mixture is placed on a Parr shaker under 345 kPa of hydrogen for 18 hrs. The catalyst is removed by filtration through celite and the filtrate is concentrated. TLC showed starting material still present. The residue is dissolved in ethanol (50 mL) and acetic acid (50 mL) and added to 2.0 g of 10% palladium on carbon in a Parr bottle. After 18 hrs, the mixture is filtered through celite and concentrated. The $^1$H NMR of the crude product showed complete debenzylation. To the crude product is added a dilute solution of hydrochloric acid (8 mL of concentrated hydrochloric acid in 20 mL of water) followed by ethanol (20 mL). The solution is concentrated to dryness. The residue is dissolved in hot isopropanol (100 mL) and ca. 1 g of charcoal is added. After filtering through celite, the solution is allowed to stand for 2 days. A white solid is collected, washed with isopropanol, and allowed to air-dry for two days. After 2 days in vacuum oven at 45° C., R-5-hydroxy-3-[(4-methylpiperazino)-methyl]-2,3-dihydro-2,2,4,6,7-pentamethyl-1-benzofuran dihydrochloride hydrate (9.0 g, 68%) is collected. $[\alpha]_D^{20}$ (water)=+20.9.

EXAMPLE 21

5-BENZYLOXY-2,2,4,6,7-PENTAMETHYL-2,3-DIHYDRO-1-BENZOFURAN-3-OL

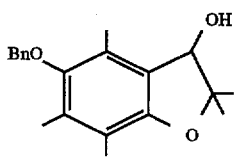

Add sodium borohydride (12.2 g, 0.324 mmol) portionwise during 45 minutes to a solution of 5-benzyloxy-2,2,4,6,7-pentamethyl-2,3-dihydro-1-benzofuran-3-one (32 g, 0.108 mmol) in methanol (300 mL). After 2 hrs quench the reaction with an aqueous solution of citric acid. Extract the solution with ethyl acetate and wash the organic layer with an aqueous solution of sodium bicarbonate and brine. Dry the organic layer on sodium sulfate and concentrate to give 5-benzy! oxy-2,2,4,6,7-pentamethyl-2,3-dihydro-1-benzofuran-3-ol as a white solid (28 g, 83%).

EXAMPLE 22

5-BENZYLOXY-3-CYANO-2,2,4,6,7-PENTAMETHYL-2,3-DIHYDRO-1-BENZOFURAN

Add acetic anhydride (0.5 g, 4.8 mmol) and triethylamine (1 mL) to a solution of 5-benzyloxy-2,2,4,6,7-pentamethyl-2,3-dihydro-1-benzofuran-3-ol (1.0g , 3.2 mmol) and

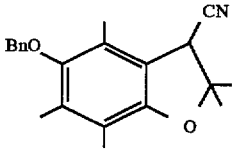

dimethyl aminopyridine (10 mg) in methylene chloride (15 mL). Stir the mixture during one hour. Quench the reaction with an aqueous solution sazurated in sodium bicarbonate. Separate the organic layer and wash successively with aqueous solutions of acetic acid, sodium bicarbonate, and brine. Dry over sodium sulfate and concentrate to give an oil. Solidify the 5-benzyloxy-3-acyloxy-2,2,4,6,7-pentamethyl-2,3-dihydro-1-benzofuran in the freezer (1.03 g, 91%).

Add diethtylaluminium cyanide (1.2 mL, 1.2 mmol) to a solution of 5-benzyloxy-3-acyloxy-2,2,4,6,7-pentamethyl-2,3-dihydro-1-benzofuran (0.4 g) in toluene (5 mL). Stir the solution during one hour, quench the reaction with an aqueous solution of potassium hydroxyde and extract with toluene. Wash the organic layer with an aqueous solution of sodium bicarbonate and brine. Dry the organic layer over sodium sulfate and evaporate the solvent to obtain 5-benzyloxy-3-cyano-2,2,4,6,7-pentamethyl-2,3-dihydro-1-benzofuran as a white solid (0.35 g, 90%).

EXAMPLE 23

5-BENZYLOXY-2,2,4,6,7-PENTAMETHYL-2,3-DIHYDRO-1-BENZOFURAN-3-CARBOXYLIC ACID

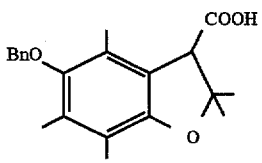

Add an aqueous solution of potassium hydroxyde 10% (5 mL) and hydrogen peroxide 30% (5 mL) to a solution of 5-benzyloxy-3-cyano-2,2,4,6,7-pentamethyl-2,3-dihydro-1-benzofuran (300 mg). After stirring for 15 min at room temperature, heat the solution under reflux during 3 days. Cool the solution to room temperature and extract with methylene chloride. Wash the organic layer with brine and dry over sodium sulfate. Concentrate the solution to give a solid which is dissolved in dioxane (5 mL) and treated with hydrochloric acid (5 mL). Heat the solution under reflux during two hrs. Cool the mixture to room temperature and extract with ethyl acetate. Wash the ethyl acetate solution with brine and dry over sodium sulfate. Concentrate the solution to obtain 5-benzyloxy-2,2,4,6,7-pentamethyl-2,3-dihydro-1-benzofuran-3-carboxylic acid as an oil (206 mg, 65%).

The compounds of this invention are free radical scavengers as disclosed in Patent Application WO93/20057, filed Mar. 10, 1993 and U.S. counterpart U.S. Ser. No. 08/318,633, filed Dec. 22, 1994. Free radical reactions have been implicated in the pathology of more than 50 human diseases. Radicals and other reactive oxygen species are formed constantly in the human body both by deliberate synthesis (e.g. by activated phagocytes)and by chemical side-reactions. They are removed by enzymic and non enzymic antioxidant defense systems. Oxidative stress, occurring when anti-oxidant defenses are inadequate, can damage lipids, proteins, carbohydrates and DNA. A few clinical conditions are caused by oxidative stress, but more often the stress results from the disease and can make a significant contribution to the disease pathology. For a more detailed review see B. Halliwell in *Drugs*, 1991, 42, 569–605.

There is a growing body of information that suggests a pathophysiologic role of oxygen free-radical-mediated lipid peroxidation following central nervous system trauma or stroke, either ischemic or hemorrhagic. A reduction in cerebral tissue concentration of endogenous antioxidants has been observed, as well as an increase in lipid peroxidation products. Inhibitors of brain lipid peroxidation counteract and reduce cerebral tissue damage, as well as to prolong life of traumatized animals. These findings have been reviewed by E. D. Hall and J. M. Braughler in *Free Radical Biology and Medicine*, 1989, 6, 303–313 and elsewhere. M. Miyamoto et al., (*J. Pharmacol. Exp. Ther.*, 1989, 250, 1132) report that neurotoxicity due to excessive glutamic acid release is similarly reduced by antioxidants. They suggest the use of agents that inhibit brain lipid peroxidation for treatment of neurodegenerative diseases such as Huntington's and Alzheimer's disease in which excessive glutamic acid release has been observed. M. R. Hori et al., (*Chem. Pharm. Bull.* 1991, 39, 367) report on anti-amnesic activity of brain lipid peroxidation inhibitors in rats.

The role of oxygen free radicals in Parkinson's disease has been reviewed recently (*Free Radical Biol Med.*, 1991, 10, 161–169) and a free radical scavenger has been tested clinically with some success (*Fundam. Clin. Pharmacol.* 1988, 2, 1–12).

Ischemia followed by reperfusion causes formation of oxygen-derived free radicals and increased lipid peroxidation and results in tissue injury. Administration of free radical scavengers to animals subjected to ischemia/reperfusion reduces these effects in heart, lung, kidney, pancreas, brain and other tissues.

The process of inflammation is also known to involve the release of superoxide radicals from phagocytic cells which cause some of the symptoms of rheumatoid arthritis and other inflammatory diseases such as ulcerative coiliris. Free radicals scavengers, such as the compounds of this invention, are also useful in treatment of these diseases.

Smoke inhalation leads to lung injury due to an increase in pulmonary microvasculature and pulmonary edema. This process is accompanied by increased lipid peroxidation in lung tissue. An inhibitor of lipid peroxidation was shown to reduce these symptoms in animals subjected to hot sawdust smoke by Z. Min et al., (*J. Med. Cell. PLA*, 1990, 5, 176–80). They suggest the use of antioxidants in treatment of smoke inhalation-lung injury, adult respiratory distress syndrome and emphysema.

Reactive oxygen species also play a role in the formation of foam cells in artherosclerotic plaques (reviewed by D. Steinberg et al., *New Engl. J. Med.*, 1989, 320, 915–924) and the free radical scavenger probucol has a marked antiartherosclerotic effect in hyperlipidemic rabbits (Carew et al., *Proc. Natl. Acad. Sci. USA*, 1987, 84, 7725–7729). Degenerative retinal damage and diabetogenic retinopathy have also been listed as target for treatment with free radical scavengers (cf. J. W. Baynes, *Diabetes*, 1991, 40, 405–412; S. P. Wolffetal., *Free Rad. Biol. Med.*, 1991, 10, 339–352).

The compounds may be also useful in the treatments of cancers, and degenerative diseases related to aging, stroke, and head trauma, since oxygen-derived free radicals have been identified among causative factors for reviews, see B. Halliwell and C. Gutteridge, *Biochem. J.*, 1984, 219, 1–14; TINS 1985, 22–6. Antioxidants have also been shown to be useful in the treatment of cataracts, *Free Rad. Biol. Med.*, 12:251–261 (1992).

In vitro and in vivo activity for the compounds of this invention may be determined by the use of standard assays which demonstrate the free radical scavenging property, affinity for cardiac tissue and cardioprotective properties, as well as by comparison with agents known to be effective for these purposes. Exemplary of the assay useful for determining the free-radical scavenging property of the compounds of this invention is by the in vitro inhibition of lipid peroxidation in rat brain homogenates.

The free radical scavenging properties of the compounds may readily be evaluated using standard and recognized procedures utilized in the art. For example the free radical scavenging property may be evaluated by an assay wherein superoxide radicals are generated by 4 mU of xanthine oxidase in the presence of 0.1 mM xanthine and detected by reduction of 40 μm nitro blue tetrazolium (NBT) to the diformazan dye in a spectrophotometric assay as described by C. Beauchamp and I. Fridovick, (*Analyt. Biochem.* 1971, 44, 276–287). The 30 U of superoxide dismutase inhibited this reduction by 90% which is due to superoxide radicals. In the presence of a superoxide scavenger (test compound) there is a competition for the superoxide radical and thus a reduction in the color formation of NBT demonstrates the superoxide radical scavenging property of the test compound.

Inhibiting the process of lipid peroxidation may be assayed using tissue homogeneates for measuring the antioxidant activity of biological fluids by the methodology of J. Stocks et al., (Clin. Sci. Mol. Med., 1974, 47, 215–222), wherein a brain tissue homogeneate of treated adult Sprague Dawley rats is utilized.

Samples of total volume 1 mL of diluted brain homogenate and with the scavenger at an appropriate dilution are incubated. Non-incubated samples are taken as background. Controls are run without scavenger and a sample containing only buffer is taken as blank. After incubation at 37° C. for 30 min, 200 µL of 35% perchloric acid is added, the samples centrifuged and 800 µL of the supernatants mixed with 200 µL of thiobarbituric acid reactive material is developed at 100° C. in a boiling water bath for 15 min, and absorbance read at 532 nm.

For ex vivo inhibition of tissue including heart or brain tissue, lipid peroxidation in mice may be utilized to demonstrate the ability of the compounds to penetrate and act as free radical scavengers in the brain. This assay involves pretreatment of male CDI mice by subcutaneous administration of the test compound. One hour later the brains are excised, homogenized 1+9 (w/v) in 20 mM potassium phosphate buffer at pH 7.3 (0.14M KCl) and incubated at 1/100 concentration in 1 mL of buffer at 37° C. for 30–120 min. At the end of the incubation 200 µL of 35% perchloric acid is added and proteins removed by centrifugation. To 800 mL of the supernatant are added 200 µL of 1% TBA and the samples are treated to 100° C. for 15 min. The TBA-adduct is extracted into 2 times 1 mL of n-butanol. The fluorescence is measured at an excitation wavelength of 515 nm and an emission wavelength of 553 nm against a standard prepared from malondialdehyde dimethylacetal.

Stimulated human leukocytes release radicals and other oxygen metabolites, which, during inflammation, act as a microbial agents. At the same time, they release proteolytic enzymes, such as elastase, which are also microbicidal but potentially threaten the connective tissue of the host. An endogenous $\alpha_1$-proteinase inhibitor ($\alpha_1$Pi) normally protects the host tissue from protelytic digestion. The $\alpha_1$Pi is however, inactivated by the leukocyte-derived oxidants. Antagonism of $\alpha_1$Pi is an indication of the disclosed radical scavengers. The concentration needed to protect 50% of the elastase inhibitory capacity of $\alpha_1$Pi ($PC_{50}$) depends on the amount of stimulated leukocytes present.

Method: The procedure described by Skosey and Chow was followed (see J. L. Skosey and D. C. Chow in Handbook of Methods for Oxygen Radical Research (Greenwald, R. A., ed.) 1985, 413–416, CRC Press, Boca Raton). In short, human $\alpha_1$Pi was incubated with zymosan-stimulated human peripheral-blood leukocytes in the presence or the absence of the scavengers. The amount of $\alpha_1$Pi protected from oxidative inactivation was determined by its residual elastase inhibitory capacity.

The relevance to inflammation matter has been reviewed by Weiss (see S. J. Weiss, N. England J. Med. 1989,320, 365–376). Lung emphysema is associated with a genetic defect in $\alpha_1$Pi; the disease is further enhanced by oxidants inhaled during cigarette smoking, which leads to oxidative inactivation of $\alpha_1$Pi in the lung tissue (see J. Travis and G. S. Salvesen, Annu. Rev. Biochem.,1983, 52, 655–709). Oxidized $\alpha_1$Pi has also been isolated from rheumatoid synovial fluid (see P. S. Wong and J. Travis, Biochem. Biophys Roc. Commun. 1980, 06, 1440–1454). The degradation of hyaluronic acid, a macromolecule accounting for the viscosity of synovial fluid, is triggered by superoxyl radicals released from human leukocytes in vitro (see R. A. Greenwald and S. A. Moak, Inflammation, 1986, 10, 15–30). Furthermore, nonsteroidal anti-inflamatory drugs were shown to inhibit the release of superoxyl radicals from leukocytes (see H. Strom and I. Ahnfelt-Ronne, Agents and Actions, 1989, 26, 235–237 and M. Roch-Arveiller, V. Revelant, D. Pharm Huy, L. Maman, J. Fontagne J. R. J. Sorenson and J. P. Giroud, Agents and Actions, 1990, 31, 65–71), and 5-aminosalicylic acid may exert its therapeutic activity in inflammatory bowel disease by radical scavenger mechanism (see I. Ahnfelt-Ronne, O. H. Nielsen, A. Christensen, E. Langholz, V. Binder and P. Riis, Gastroenterology, 1990, 98, 1162–1169). Therefore, it is believed that the compounds of this invention may be useful in the mentioned pathologic situations and that inflammatory bowel disease may be a special target. An immune stimulatory effect of antioxidants has also been reported in that they enhanced lymphocyte activity (R. Anderson and P. T. Lukey, Ann. N.Y. Acad. Sci., 1987,498, 229–247) in vitro in the presence of triggered leukocytes, and exvivo after pretreatment of human volunteers.

Thus, using standard and well known methodology, as well as by comparison with known compounds found useful, it is to be found that the compounds are free radical scavengers useful in the prevention and treatment of such disease states related to neurotoxicity due to excessive glutamine release, to Huntington's disease, Alzheimer's disease and other cognitive dysfunctions, (e.g. memory, learning and attention deficits), amnesia, and Parkinson's disease, as well as treatment and prevention of tissue damage in heart, lung, kidney, pancreas and brain tissues induced by ischemia/reperfusion, and to allay acute blood loss due to hemorrhagic shock.

The compounds of the present invention are of particular interest in treating patients with stroke, nervous system trauma, and reperfusion damage. As used herein, these terms have the following meanings:

a) stroke means cerebrovascular disease which includes cerebral insufficiency due to transient disturbances of blood flow, infarction, and arteriovenous malformation which causes symptoms of mass lesion, infarction or hemorrhage.

b) nervous system trauma means injury to the head or spine. For example, injury can occur from skull or spine penetration or from rapid brain acceleration or deceleration which injures tissue at the point of impact, at its opposite pole or within the frontal or temporal lobes. Injury may consist of nerve tissue, blood vessels and/or meninges damage resulting in neural disruption, ischemia and/or edema.; and c) reperfusion damage means the damage that occurs in any blood-deprived tissue, anywhere in the body, upon reintroduction of the blood supply. For example, reperfusion of an ischemic area of the myocardium or the cerebrum.

The compounds of this invention can be utilized both prophylatically and therapeutically. The amount of active ingredient for therapeutic administration can vary over a wide range and is dependent upon such factors as the species of mammal to be treated, its age, health, sex, weight, nature and severity of the condition being treated.

The term "patient" refers to a warm-blooded animal such as, for example, rats, mice, dogs, cats, guinea pigs, primates and humans. Generally, a therapeutically effective amount of the active ingredient to be administered will range from about 0.1 mg/kg to 30 mg/kg of body weight per day. For prophylatic administration, corresponding lower doses can be utilized. Preferably, the compounds of the present invention will be administered to the patient in combination with a pharmaceutically acceptable carrier which is any substance which aids in the administration of the compound without substantially affecting its therapeutic properties.

Most preferably, the compounds are administered intravenously particularly under crisis situations wherein it is essential that the therapeutic agent be gotten to its site of action as quickly as possible, such as in those emergency conditions caused by coronary infarction, stroke and surgical interventions, conditions which can cause severe reperfusion damage.

The compounds of this invention can be orally administered, preferably using more active ingredient per day than when parenterally administered, preferably taking divided doses 3 to 4 times per day. Preferably, enteral administration in post "crisis" situations, particularly after being released from hospitalized conditions. The compounds can be used in standard dosage unit forms such as tablets, capsules, dragees, lozenges, elixirs, emulsions, suspensions, and in cases wherein topical application is preferred by suppository or sub-lingual administration. Tablets and capsules containing from 100 mg to 400 mg of active ingredient are preferred modes of enteral administration. Of course, in the treatment of inflammation the preferred method of administration is by depot injection directly to the situs of the inflammation area with follow-up enteral means of administration.

In preparing solid dose forms such as tablets, the active ingredient is generally blended with conventional pharmaceutical carriers or excipients such as gelatin, various starches, lactose, calcium phosphate or powdered sugar. The term pharmaceutical carrier as used herein also includes lubricants employed to improve the flow of tablet grannulations and which prevent adhesion of tablet material to the surfaces of tablet dies and punches. Suitable lubricants include for example, talc static acid, calcium stearate, magnesium stearate and zinc stearate. Also included within the definition of a pharmaceutical carrier as used herein, are disintegrating agents added to assist the breakup and dissolution of tablets following administration, as well as coloring and/or flavoring agents to enhance the aesthetic qualities of the tablets and make them more acceptable to the patient.

Suitable liquid excipients for the preparation of liquid dosage unit forms include water and alcohols such as ethanol, benzyl alcohol and the polyethylene glycols, either with or without the addition of a surfactant. In general, the preferred liquid excipients, particularly for injectable preparations, include water, physiological and saline solutions, dextrose and glycol solutions such as an aqueous propylene glycol or polyethylene glycol solutions. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to 15% by weight. The surfactant can be single component having the above-identified HLB, or a mixture of two or more components having the desired HLB. Illustrative of surfactants useful in parenteral formulations are the class of polyoxyethylene sorbitan fatty acid esters as, for example, sorbitan monooleate and the high molecular weights adducts of ethylene oxide with a hydrophobic base, formed by the condensation of propylene oxide with propylene glycol. In certain topical and parenteral preparations, various oils can be utilized as carrier or excipients. Illustrative of such oils are minerals oils, glyceride oils such as lard oil, cod liver oil, peanut oil, sesame oil, corn oil and soybean oil. For insoluble compounds, suspending agents may be added as well as agents to control the viscosity, as for example, magnesium aluminum silicate or carboxymethyl-cellulose. In addition to these excipients, buffers, preservatives and emulsifying agents may be also be added. Typical enema preparation of the retention type enema utilize small volumes, generally much less than about 150 mL for an adult, typically volumes of only a few milliliters are preferred. Excipients and solvents for use in retention anemas should, of course, be selected so as to avoid colonic irritation and should be also selected so as to minimize absorption of the various agents.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in a contact with the skin or mucosa of the recipient. If the active agent is absorbed through the skin, a controlled and predetermined flow of the active agent is administrated to the recipient. In the case of microcapsules, the encapsuling agent may also function as the membrane.

In another device for transdermallly administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

The compounds of the present invention may be incorporated into an aerosol preparation by means commonly known to those skilled in the art. The aerosol preparation may be prepared for use as a topical aerosol or may be prepared for inhalation. The aerosol preparation may be in the form of a solution or a suspension and may contain other ingredients such as solvents, propellants and/or dispersing agents. Typical examples of aerosol preparations are shown in *Remington's Pharmaceutical Sciences,* 18th ed., Mack Publishing Company, Easton Pa., pp. 1694–1712 (1990) incorporated herein by reference.

As it is true for most classes of compounds suitable or use as therapeutic agents certain subclasses and certain specific compounds are more preferred than others. In this instance it is preferred that the $R_2$, $R_4$, $R_6$ and $R_7$ moieties be methyl.

Preferably $R_5$ is H or an acyl moiety including formyl and acetyl. X is preferably $CH_2A$. A is preferably

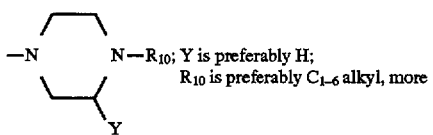
Y is preferably H;
$R_{10}$ is preferably $C_{1-6}$ alkyl, more preferably $C_{1-3}$ alkyl and more preferably methyl. Other preferred forms of $R_{10}$ are acyloxyalkylene, especially —$CH_2$—O—$C(O)CH_3$, hydroxyalkyl ($C_{2-6}$) especially —$(CH_2)_2$—OH, and pyrimidinyl.

What is claimed is:

1. A process for preparing 2,3-dihydro-benzofuranol derivatives of formula (I)

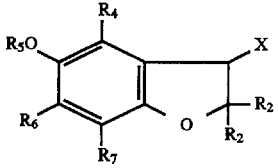

including stereoisomers, enantiomers, optically active and racemic mixtures thereof, or their pharmaceutically acceptable salts thereof, wherein $R_2$ is $C_{1-4}$ alkyl each $R_2$ moiety being independently $C_{1-4}$ alkyl or both $R_2$ moieties, when taken together with the carbon atom to which they are attached, form a $C_{5-6}$ cyclic hydrocarbyl moiety;

$R_4$ is $C_{1-6}$ alkyl;

$R_5$ is H or C(O)R with R being H or $C_{1-9}$ alkyl;

$R_6$ is $C_{1-6}$ alkyl;

$R_7$ is H or $C_{1-6}$ alkyl;

X is $COOR_8$, $CH_2OH$, halomethyl, C(O)A or $CH_2A$;

A is $NR_7R_9$, $-N^\oplus R_6R_6R_6-Q^\ominus$, pyrrolidino, piperidino, morpholino, or 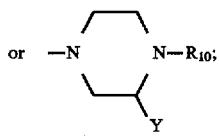

$R_8$ is H, $C_{1-6}$alkyl, or -$(CH_2)_m$-A with m being 2,3 or 4;

$R_9$ is

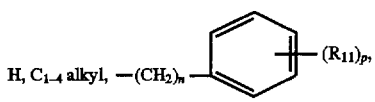

n is 1, 2, 3 or 4, p is 1, 2, or 3;

$R_{10}$ is H, $C_{1-8}$ alkyl, $C_{2-6}$ alkenyl, $C_{4-6}$ cycloalkyl, cyclohexylmethyl, hydroxyalkyl ($C_{2-6}$), dihydroxyalkyl ($C_{3-6}$), $C_{2-9}$ acyloxyalkyl ($C_{2-6}$), $C_{1-4}$ alkoxyalkyl ($C_{1-6}$),

-$(CH_2)_{2-6}$-O-$(CH_2)_{2-4}$-OH,

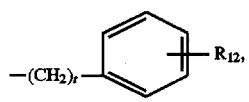

t being 0, 1 or 2, or pyrimidinyl, with the proviso that when Y is other than H then $R_{10}$ is H;

Y is H, $CH_3$ or $COOR_7$;

$R_{11}$ is H, $C_{1-4}$ alkoxy, $C_{1-4}$ alkyl or halogeno;

$R_{12}$ is ortho $C_{1-4}$ alkoxy, ortho $C_{1-4}$ alkyl or p-halo; and

Q is a halide, or sulfonate ion $^\ominus$—$SO_3R_1$ with $R_1$ being H, $C_{1-6}$ alkyl, aryl or aralkyl, comprising the steps of:

(a) reacting a hydroquinone of formula (3) wherein $R_4$, $R_6$ and $R_7$ are defined above and Pg is hydrogen or a suitable protecting group,

with a 2-halogeno-2-($C_{1-4}$)alkyl($C_{1-6}$)acylhalide or a 2-halogeno-2-($C_{1-4}$)alkyl($C_{1-6}$)acid of formula $R_2$-C(W)($R_2$)C(O)V wherein $R_2$ is as defined above, W is halogen such as iodide, bromide, chloride or fluoride and more preferably bromide or chloride and V is halogen as defined above or hydroxy (—OH) using Friedel-Crafts reaction conditions, optionally saponifying or deprotecting the so-produced compound, thereby producing a benzofuranone of formula (6), wherein $R_2$, $R_4$, $R_6$ and $R_7$ are as defined above,

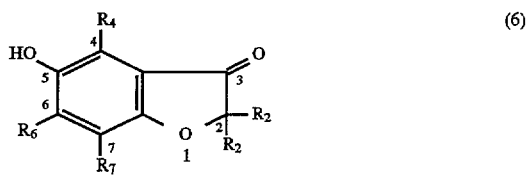

(b) protecting the 5-hydroxy moiety of so-produced benzofuranone (6) with a suitable protecting group and converting the ketone moiety to exo-methylene moiety thereby producing the benzofuran of formula (8), wherein $R_2$, $R_4$, $R_6$ and Pg are as defined above,

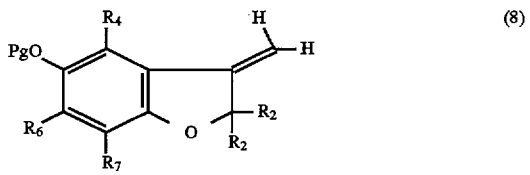

(c) converting by hydroboration/oxidation the exo-methylene group of the so-produced benzofuran (8) into 3-hydroxymethyl group thereby producing compound of formula (9) wherein $R_2$, $R_4$, $R_6$, $R_7$ and Pg are as defined above,

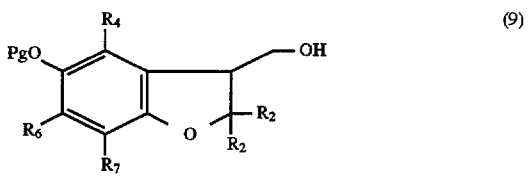

optionally, (d) resolving the alcohol (9) to obtain the (R) and (S) optically active compounds (9), optionally, (e) deprotecting the 5-hydroxy group of compound (9), thereby producing the benzofuranol of formula (I) wherein X is $CH_2OH$ and $R_5$ is H, optionally, (f) oxidizing 3-hydroxymethyl of compound (9) into 3-carboxylic acid of formula (12)

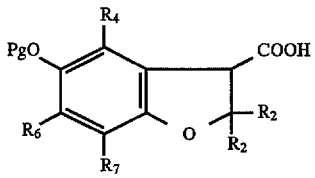
(12)

optionally, (g) resolving the racemic acid of formula (12) to obtain the (S) and (R) optically active compounds (12), optionally, (h) deprotecting the 5-hydroxy group of the acid (12), thereby producing the benzofuranol of formula (I) wherein X is COOH and $R_5$ is H, optionally, (i) esterifying the carboxylic acid of formula (12) and optionally deprotecting the hydroxy group, thereby producing the benzofuranol of formula (I) wherein X is $COOR_8$ and $R_5$ is H, optionally, (j) reacting the desired amino group with the carboxylic acid of formula (12) and optionally deprotecting the hydroxy group, thereby producing the benzofuranol of formula (I) wherein X is C(O)A and $R_5$ is H, optionally, (k) reducing the carboxylic acid (12) thereby producing compound of formula (9), optionally, (l) optionally deprotecting the hydroxy of compound (9) and converting the hydroxy of the 3-hydroxymethyl group to an halogen, thereby producing the benzofuranol of formula (I) wherein X is halomethyl and $R_5$ is H, optionally, (m) deprotecting optionally the hydroxy group of compound (9) and converting the hydroxy of the 3-hydroxymethyl group to a leaving group, thereby producing the benzofuranol of formula (10),

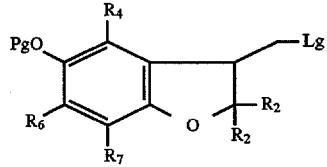
(10)

(n) substituting the leaving group of compound (10) by desired amino group and deprotecting optionally the hydroxy group to obtain the product of formula (I) wherein X is $CH_2A$ and $R_5$ is H, optionally, (o) esterifying the 5-hydroxy group of compound of formula (I) wherein $R_5$ is H, to give compound of formula (I) wherein $R_5$ is C(O)R, R being $C_{1-9}$ alkyl and optionally converting said product to pharmaceutically acceptable salt thereof.

2. A process according to claim 1 for preparing 2,3-dihydro-benzofuranol derivatives of formula (I)

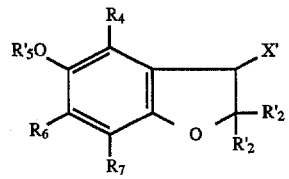
(I)

including stereoisomers, enantiomers, optically active and racemic racemic mixtures thereof, or their pharmaceutically acceptable salts thereof, wherein $R'_2$ is $C_{1-4}$ alkyl each $R'_2$ moiety being independently $C_{1-4}$ alkyl;

$R_4$ is $C_{1-6}$ alkyl;

$R'_5$ is H;

$R_6$ is $C_{1-6}$ alkyl;

$R_7$ is H or $C_{1-6}$ alkyl;

X' is $CH_2A'$, A' is

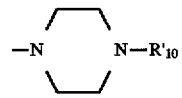

$R_{10}$ is H, $C_{1-3}$ alkyl, comprising the steps of:

(a) reacting a hydroquinone of formula (3) wherein $R_4$, $R_6$ and $R_7$ are defined above and Pg is hydrogen or a suitable protecting group,

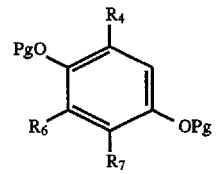
(3)

with a 2-halogeno-2-($C_{1-4}$)alkyl($C_{1-6}$)acylhalide or a 2-halogeno-2-($C_{1-4}$)alkyl($C_{1-6}$)acid of formula $R_2$-C(W)($R_2$)C(O)V wherein $R_2$ is as defined above, W is hydrogen or halogen such as iodide, bromide, chloride or fluoride and more preferably bromide or chloride and V is halogen as defined above or hydroxy (—OH) using Friedel-Crafts reaction conditions, optionally saponifying or deprotecting the so-produced compound, thereby producing a benzofuranone of formula (6), wherein $R_2$, $R_4$, $R_6$ and $R_7$ are defined as above

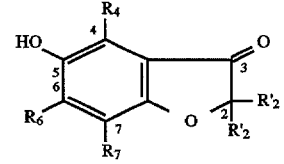
(6)

(b) protecting the 5-hydroxy moiety of so-produced benzofuranone (6) with a suitable protecting group and converting the ketone moiety to exo-methylene moiety thereby producing the benzofuran of formula (8), wherein $R'_2$, $R_4$, $R_6$, $R_7$ and Pg are as defined above,

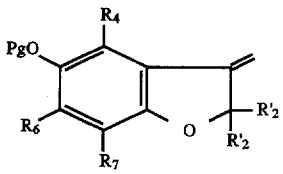

(c) converting by hydroboration/oxidation the exo-methylene group of the so-produced benzofuran (8) into 3-hydroxymethyl thereby producing compound of formula (9), wherein R'$_2$, R$_4$, R$_6$, R$_7$ and Pg are as defined above,

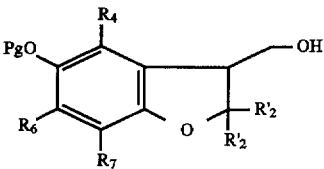

optionally, (d) resolving the alcohol (9) to obtain the (R) and (S) optically active compounds (9), optionally, (e) oxidizing 3-hydroxymethyl of compound (9) into 3-carboxylic acid of formula (12)

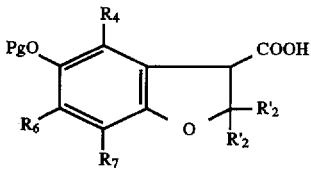

optionally, (f) resolving the racemic acid of formula (12) to obtain the (R) and (S) optically active compounds (12), (g) reducing the carboxylic acid (12) thereby producing compound of formula (9), (h) optionally deprotecting the hydroxy group of compound (9) and converting the hydroxy of the 3-hydroxymethyl group to a leaving group, thereby producing the benzofuranol of formula (10), (i) substituting the leaving group of compound (10) by the desired amino group and optionally deprotecting the hydroxy group to obtain the product of formula (I) wherein X' is CH$_2$A',

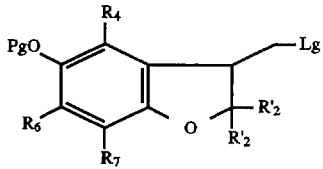

and optionally converting said product to pharmaceutically acceptable salt thereof.

3. A process according to claim 1 for preparing 2,3-dihydro-benzofuranol derivatives of formula (I)

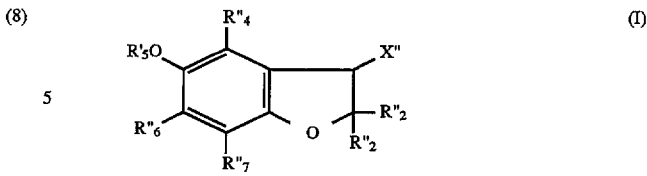

including stereoisomers, enantiomers, optically active and racemic mixtures thereof, or their pharmaceutically acceptable salts thereof, wherein R"$_2$, R"$_4$, R"$_6$ and R"$_7$ are methyl,
R'$_5$ is H,
X" is CH$_2$A", A" is

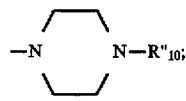

and
R"$_{10}$ is methyl,
comprising the steps of:

(a) reacting the hydroquinone of formula (3) wherein R$_4$, R$_6$ and R$_7$ are defined above and Pg is hydrogen or a suitable protecting group,

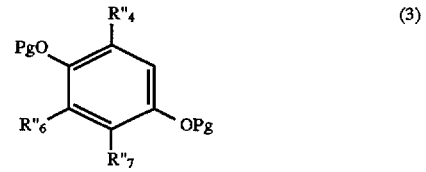

with a 2-halogeno-2-methylpropylhalide or a 2-halogeno-2-methylpropylacid using Friedel-Crafts reaction, optionally saponifying or deprotecting the so-produced compound, thereby producing the benzofuranone of formula (6), wherein R"$_2$, R"$_4$, R"$_6$ and R"$_7$ are as defined above,

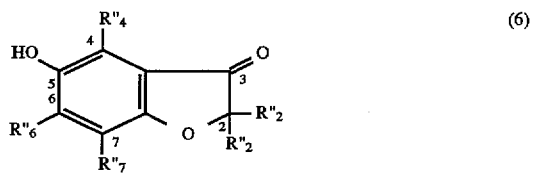

(b) protecting the hydroxy moiety of so-produced benzofuranone (6) with a suitable protecting group and converting the ketone to exo-methylene moiety thereby producing the benzofuran of formula (8), wherein R"$_2$, R"$_4$, R"$_6$, R"$_7$ and Pg are as defined above,

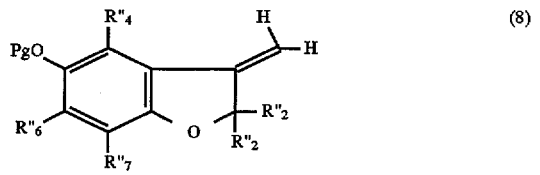

(c) converting by hydroboration/oxidation the exo-methylene group of the so-produced benzofuran (8) into 3-hydroxymethyl group thereby producing compound of formula (9),

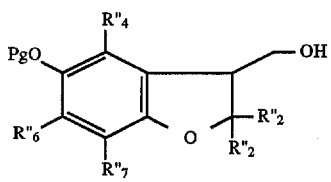 (9)

optionally, (d) resolving the alcohol (9) to obtain the (R) and (S) optically active isomers, optionally, (e) oxidizing 3-hydroxymethyl of compound (9) into 3-carboxylic acid of formula (12)

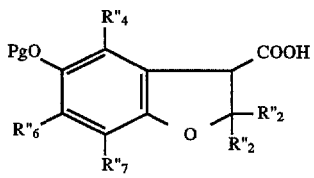 (12)

optionally, (f) resolving the racemic acid of formula (12) to obtain the (R) and (S) optically active compounds (12), optionally, (g) reducing the carboxylic acid (12) thereby producing compound of formula (9), optionally, (h) optionally deprotecting the hydroxy group of compound (9) and converting the hydroxy of the 3-hydroxymethyl group to a leaving group, thereby producing the benzofuranol of formula (10),

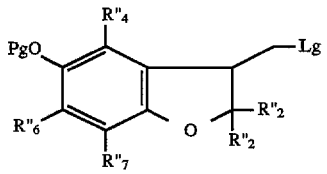 (10)

(i) substituting the leaving group of compound (10) by the desired amino group and optionally deprotecting the hydroxy group to obtain the product of formula (I) wherein X" is $CH_2A$", and optionally converting said product to pharmaceutically acceptable salt thereof.

4. A process according to claim 3 for preparing 2,3-dihydro-benzofuranol derivatives of formula (I)

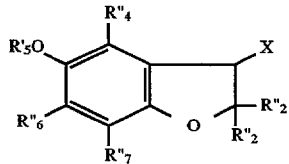 (I)

including stereoisomers, enantiomers, optically active and racemic mixtures thereof, or their pharmaceutically acceptable salts thereof, wherein $R"_2$, $R"_4$, $R"_6$ and $R_7$ are methyl,
$R'_5$ is H, X" is $CH_2A$", "A is

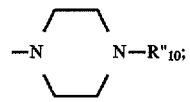

and
$R"_{10}$ is methyl,
comprising the steps of:

(a) reacting the hydroquinone of formula (3) wherein $R_4$, $R_6$ and $R_7$ are defined above and Pg is hydrogen or a suitable protecting group,

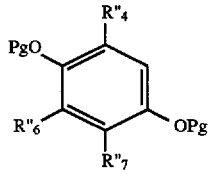 (3)

with a 2-halogeno-2-methylpropylhalide or a 2-halogeno-2-methylpropylacid using Friedel-Crafts reaction, optionally saponifying or deprotecting the so produced compound, thereby producing the benzofuranone of formula (6) wherein $R"_2$ is defined above,

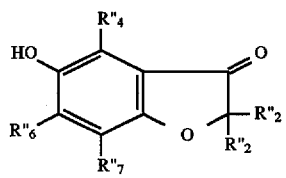 (6)

(b) protecting the hydroxy moiety of so-produced benzofuranone (6) with a suitable protecting group and converting the ketone to exo-methylene moiety thereby producing the benzofuran of formula (8),

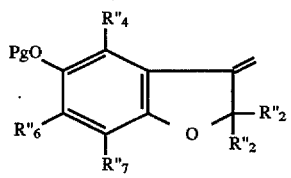 (8)

(c) converting by hydroboration/oxidation the exo-methylene group of the so-produced benzolutah (8) into 3-hydroxymethyl group thereby producing compound of formula (9),

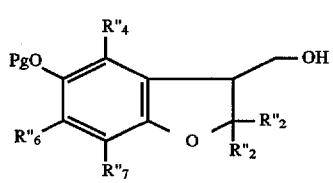 (9)

optionally, (d) resolving the alcohol (9) to obtain the (R) and (S) optically active isomers, (e) optionally deprotecting the hydroxy group of compound (9) and converting the hydroxy of the 3-hydroxymethyl group to a leaving group, thereby producing the benzofuranol of formula (10),

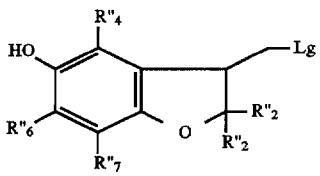 (10)

(f) substituting the leaving group of compound (10) by the desired amino group to obtain the product of formula (I) wherein X" is CH$_2$A", and optionally converting said product to pharmaceutically acceptable salt thereof.

5. A process for resolving into its optically active isomers compound of formula (9)

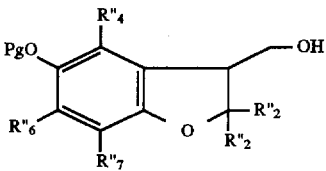 (9)

wherein

R"$_2$, "R$_4$, R"$_6$ and R"$_7$ are methyl, Pg is hydrogen or is a suitable protecting group, comprising the steps of:

(a) reacting compound of formula (9) with *lipase/candida cylindracea* and vinyl acetate, (b) separating the individual isomers, (c) optionally deprotecting the 5-hydroxy group.

6. A process according to claim 3 for preparing 2,3-dihydro-benzofuranol derivatives of formula (I)

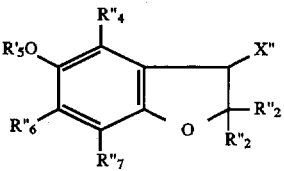 (I)

including stereoisomers, enantiomers, optically active and racemic mixtures thereof, or their pharmaceutically acceptable salts thereof, wherein R"$_2$, R"$_4$, R"$_6$ and R"$_7$ are methyl,
R'$_5$ is H,
X" is CH$_2$A", A" is

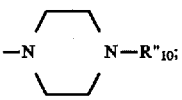

and
R$_{10}$" is methyl, comprising the steps of:

(a) reacting the quinone of formula (3) wherein R$_4$, R$_6$ and R$_7$ are defined above and Pg is hydrogen or a suitable protecting group,

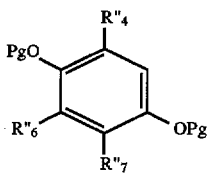 (3)

with a 2-halogeno-2-methylpropylhalide or a 2-halogeno-2-methylpropylacid using Friedel-Crafts reaction, optionally saponifying or deprotecting the so produced compound, thereby producing the furanone of formula (6) wherein R"$_2$ is defined above,

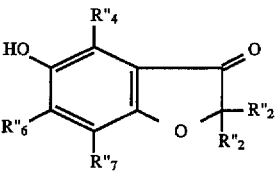 (6)

(b) protecting the hydroxy moiety of so-produced benzo-furanone (6) with a suitable protecting group and converting the ketone to exo-methylene moiety thereby producing the benzofuran of formula (8),

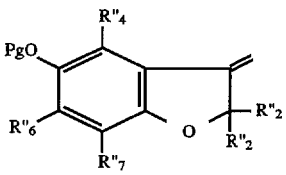 (8)

(c) converting by hydroboration/oxidation the exo-methylene group of the so-produced benzolutah (8) into 3-hydroxymethyl group thereby producing compound of formula (9),

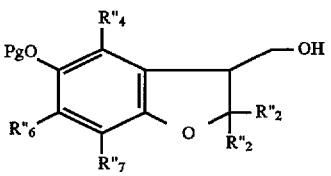 (9)

(d) oxidizing 3-hydroxymethyl of compound (9) into 3-carboxylic acid of formula (12)

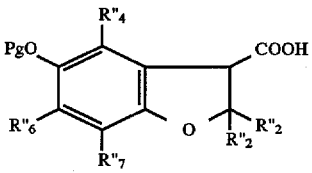 (12)

optionally, (e) resolving the racemic acid of formula (12) to obtain the (R) and (S) optically active compounds (12), (f) Reducing the carboxylic acid (12) thereby producing compound of formula (9), (g) optionally deprotecting the hydroxy group of compound (9) and converting the hydroxy of the 3-hydroxymethyl group to a leaving group, thereby producing the benzofuranol of formula (10),

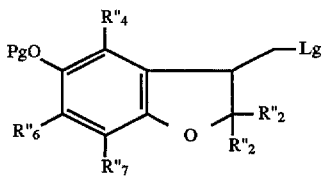
(10)

(h) substituting the leaving group of compound (10) by the desired amino group optionally deprotecting the hydroxy group to obtain the product of formula (I) wherein X" is $CH_2A$".

and optionally converting said product to pharmaceutically acceptable salt thereof.

7. A process for preparing 2,3-dihydro-benzofuranol derivatives of formula (I)

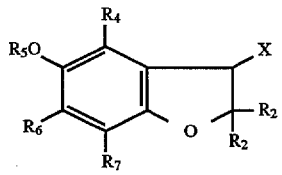
(I)

including stereoisomers, enantiomers, optically active and racemic mixtures thereof, or their pharmaceutically acceptable salts thereof, wherein $R_2$ is $C_{1-4}$ alkyl each $R_2$ moiety being independently $C_{1-4}$ alkyl or both $R_2$ moieties, when taken together with the carbon atom to which they are attached, form a $C_{5-6}$ cyclic hydrocarbyl moiety;

$R_4$ is $C_{1-6}$ alkyl;

$R_5$ is H or C(O)R with R being H or $C_{1-9}$ alkyl;

$R_6$ is $C_{1-6}$ alkyl;

$R_7$ is H or $C_{1-6}$ alkyl;

X is $COOR_8$, $CH_2OH$, halomethyl, C(O)A or $CH_2A$;

A is $NR_7R_9$, $-N^{\oplus}R_6R_6R_6-Q^{\ominus}$, pyrrolidino, piperidino, morpholino,

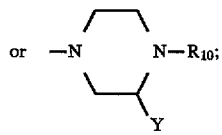

$R_8$ is H, $C_{1-6}$ alkyl, or $-(CH_2)_m-A$ with m being 2,3 or 4;
$R_9$ is H, $C_{1-4}$ alkyl,

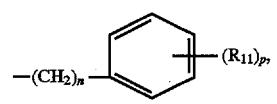

n is 1, 2, 3 or 4, p is 1, 2, or 3;

$R_{10}$ is H, $C_{1-8}$ alkyl, $C_{2-6}$ alkenyl, $C_{4-6}$ cycloalkyl, cyclohexylmethyl, hydroxyalkyl ($C_{2-6}$), dihydroxyalkyl ($C_{3-6}$), $C_{2-9}$ acyloxyalkyl ($C_{2-6}$), $C_{1-4}$ alkoxyalkyl ($C_{1-6}$),

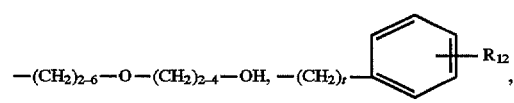

t being 0, 1 or 2, or pyrimidinyl, with the proviso that when Y is other than H then $R_{10}$ is H;

Y is H, $CH_3$ or $COOR_7$;

$R_{11}$ is H, $C_{1-4}$ alkoxy, $C_{1-4}$ alkyl or halogeno;

$R_{12}$ is ortho $C_{1-4}$ alkoxy, ortho $C_{1-4}$ alkyl or p-halo; and

Q is a halide, or sulfonate ion $^{\ominus}-SO_3R_1$ with $R_1$ being H, $C_{1-6}$ alkyl, aryl or aralkyl, comprising the steps of:

(a) reacting a quinone of formula (3) wherein $R_4$, $R_6$ and $R_7$ are defined above and Pg is hydrogen or a suitable protecting group,

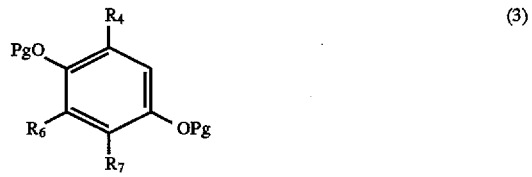
(3)

with a 2-halogeno-2-($C_{1-4}$)alkyl($C_{1-6}$)acylhalide or a 2-halogeno-2-($C_{1-4}$)alkyl($C_{1-6}$)acid of formula $R_2$-C(W)($R_2$)C(O)V wherein $R_2$ is as defined above, W is hydrogen or halogen such as iodide, bromide, chloride or fluoride and more preferably bromide or chloride and V is halogen as defined above or hydroxy (—OH) using Friedel-Crafts reaction conditions, optionally saponifying or deprotecting the so produced compound, thereby producing a furanone of formula (6), wherein $R_2$, $R_4$, $R_6$ and $R_7$ are as defined above,

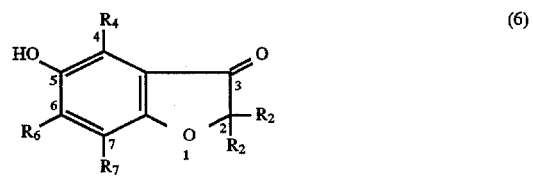
(6)

b) protecting optionally the 5-hydroxy group of the benzofurane (6), reducing the ketone into its corresponding alcohol, transforming, the 3-hydroxy group into a leaving group, substituting the leaving group by a cyano group and hydrolyzing the so-produced cyano group thereby producing the acid of formula (12)

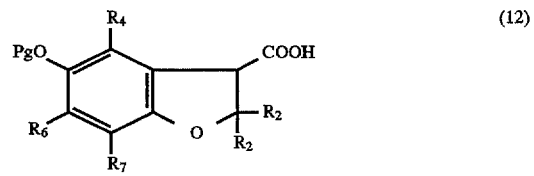
(12)

optionally, (c) resolving the racemic acid of formula (12) to obtain the (S) and (R) optically active compounds (12), optionally, (d) deprotecting the 5-hydroxy group of the acid (12), thereby producing the benzofuranol of formula (I) wherein X is COOH and $R_5$ is H, optionally, (e) esterifying the carboxylic acid of formula (12) and optionally deprotecting the hydroxy group, thereby producing the benzofuranol of formula (I) wherein X is $COOR_8$ and $R_5$ is H, optionally, (f) reacting the desired amino group with the carboxylic acid of formula (12) and optionally deprotecting the hydroxy group, thereby producing the benzofuranol of formula (I) wherein X is C(O)A and $R_5$ is H, optionally, (g) reducing the carboxylic acid (12) thereby producing compound of formula (9),

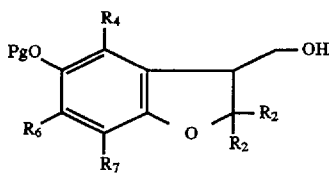

optionally, (h) optionally deprotecting the hydroxy of compound (9) and converting the hydroxy of the 3-hydroxymethyl group to an halogen, thereby producing the benzofuranol of formula (I) wherein X is halomethyl and $R_5$ is H, optionally, (i) deprotecting optionally the hydroxy group of compound (9) and converting the hydroxy of the 3-hydroxymethyl group to a leaving group, thereby producing the benzofuranol of formula (10),

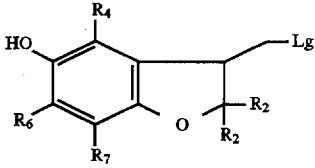

(j) substituting the leaving group of compound (10) by the desired amino group and deprotecting optionally the hydroxy group to obtain the product of formula (I) wherein X is $CH_2A$ and $R_5$ is H, optionally, (k) esterifying the 5-hydroxy group of compound of formula (I) wherein $R_5$ is H, to give compound of formula (I) wherein $R_5$ is C(O)R, and optionally converting said product to pharmaceutically acceptable salt thereof.

8. A process according to claim 7 for preparing 2,3-dihydro-benzofuranol derivatives of formula (I)

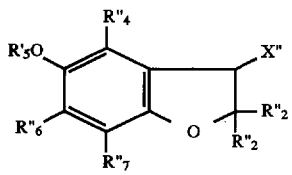

including stereoisomers, enantiomers, optically active and racemic mixtures thereof, or their pharmaceutically acceptable salts thereof, wherein $R''_2$, $R''_4$, $R''_6$ and $R''_7$ are methyl,
$R'_5$ is H,
$X''$ is $CH_2A''$, $A''$ is

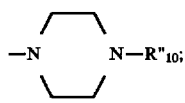

and
$R''_{10}$ is methyl,
comprising the steps of:

(a) reacting the quinone of formula (3) wherein $R_4$, $R_6$ and $R_7$ are defined above and Pg is hydrogen or a suitable protecting group,

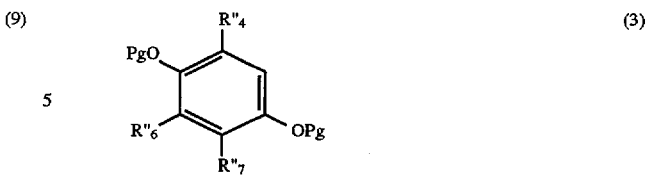

with a 2-halogeno-2-methylpropylhalide or a 2-halogeno-2-methylpropylacid using Friedel-Crafts reaction, optionally saponifying or deprotecting the so-produced compound, thereby producing the furanone of formula (6), wherein $R''_2$, $R''_4$, $R''_6$ and $R''_7$ are as defined above,

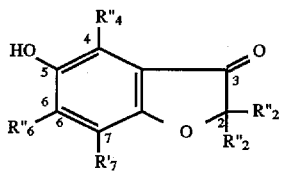

b) protecting optionally the 5-hydroxy group of the benzofurane (6), reducing the ketone into its corresponding alcohol, transforming, the 3-hydroxy group into a leaving group, substituting the leaving group by a cyano group and hydrolyzing the so-produced cyano group thereby producing the acid of formula (12)

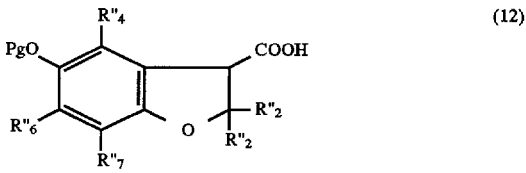

optionally, (c) resolving the racemic acid of formula (12) to obtain the (S) and (R) optically active compounds (12), (d) reducing the carboxylic acid (12) thereby producing compound of formula (9),

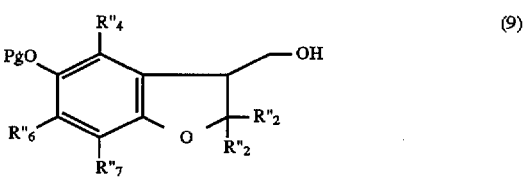

(e) deprotecting optionally the hydroxy group of compound (9) and converting the hydroxy of the 3-hydroxymethyl group to a leaving group, thereby producing the benzofuranol of formula (10),

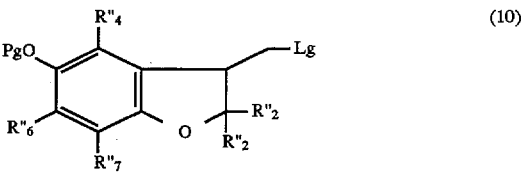

(f) substituting the leaving group of compound (10) by the desired amino group and deprotecting optionally the hydroxy group to obtain the product of formula (I) wherein X is $CH_2A$ and $R_5$ is H, and optionally converting said product to pharmaceutically acceptable salt thereof.

9. A process for preparing derivatives of formula (6)

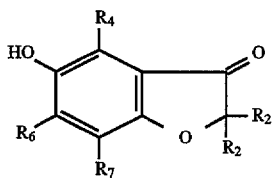
(6)

including stereoisomers, enantiomers, optically active and racemic mixtures thereof, or their pharmaceutically acceptable salts thereof, wherein $R_2$ is $C_{1-4}$ alkyl or both $R_2$ moieties, when taken together with the carbon atom to which they are attached, form a $C_{5-6}$ cyclic hydrocarbyl moiety;

$R_4$ is $C_{1-6}$ alkyl;

$R_6$ is $C_{1-6}$ alkyl; and $R_7$ is H or $C_{1-6}$ alkyl, (a) reacting the quinone of formula (3) wherein $R_4$, $R_6$ and $R_7$ are defined above and Pg is hydrogen or a suitable protecting group,

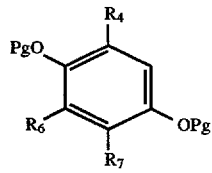
(3)

with a 2-halogeno-2-($C_{1-4}$)alkyl($C_{1-6}$)acylhalide or a 2-halogeno-2-($C_{1-4}$)alkyl($C_{1-6}$)acid of formula $R_2$-C(W)(R_2)C(O)V wherein $R_2$ is as defined above, W is hydrogen or halogen such as iodide, bromide, chloride or fluoride and more preferably bromide or chloride and V is halogen as defined above or hydroxy (—OH) using Friedel-Crafts reaction, optionally saponifying or deprotecting the so-produced compound, thereby producing the furanone of formula (6),

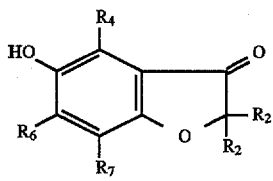
(6)

10. The compound 5-hydroxy-2,2,4,6,7-pentamethyl-2,3-dihydro-1-benzofuran-3-one.

11. The compound 5-hydroxy-3-methylene-2,2,4,6,7-pentamethyl-2,3-dihydro-benzofuran.

12. The compound 5-benzyloxy-3-hydroxymethyl-2,2,4,6,7-pentamethyl-2,3-dihydro-1-benzofuran.

13. The compound 3-hydroxymethyl-5-methoxy-2,2,4,6,7-pentamethyl-2,3-dihydro-1-benzofuran.

* * * * *

UNITED STATES PATENT AND TRADEMARK OFFICE
CERTIFICATE OF CORRECTION

PATENT NO.　:　5,698,696

DATED　　　:　16 December 1997

INVENTOR(s)　:　Gilbert Marciniak; Richard A. Schnettler; Timothy A. Ayers; Damian J. Krysan

It is certified that error appears in the above-identified patent and that said Letters Patent is hereby corrected as shown below:

Column 4, Line 42 patent reads "benzofuranol of 15 formula (10)" and should read –benzofuranol of formula (10) –.

Column 10, Line 16 patent reads "(($CH_3$)3 ...... ($OCOC_6H5$)" and should read – (($CH_3$)$_3$ .....($OCOC_6H_5$) –.

Column 10, Line 18 patent reads "(- $OCOCH_2C_6HS$)" and should read – (-$OCOCH_2C_6H_5$) –.

Column 11, Line 40 patent reads "ketene in presence" and should read – ketone in presence –.

Column 11, Line 40 patent reads "acyi halide" and should read – acyl halide –.

Column 13, Line 40 patent reads "tert-budiethylether tert-butyl methyl ether" and should read – tert-butyl methyl ether –.

Column 14, Line 5 patent reads "lipasos" and should read – lipases –.

Column 14, Line 10 patent reads "Mannhelm" and should read – Mannheim –.

Column 14, Line 12 patent reads "entrappod" and should read – entrapped –.

Column 15, Line 56 patent reads "trillate" and should read – triflate –.

UNITED STATES PATENT AND TRADEMARK OFFICE
CERTIFICATE OF CORRECTION

PATENT NO. : 5,698,696

DATED : 16 December 1997

INVENTOR(s) : Gilbert Marciniak; Richard A. Schnettler; Timothy A. Ayers; Damian J. Krysan It is certified that error appears in the above-identified patent and that said Letters Patent is hereby corrected as shown below:

Column 16, Line 52 patent reads "insitu .... dichtoromethan" and should read – in situ ......dichloromethane –.

Column 17, Line 11 patent reads "Seeyen" and should read – Seeven –.

Column 17, Line 31 patent reads "methodsbyell" and should read – methods well –.

Column 18, Line 1 patent reads "acetonitriie" and should read – acetonitrile –.

Column 19, Line 25 patent reads "oxidantas" and should read – oxidants –.

Column 19, Line 40 patent reads "the the" and should read – the –.

Column 19, Line 55 patent reads "5-hydrox" and should read – 5-hydroxy –.

Column 20, Line 44 patent reads "liltrate" and should read – filtrate –.

Column 20, Line 54 patent reads "S-(2)" and should read – S-(12) –.

Column 21, Line 13 patent reads "ChemistrX" and should read – Chemistry" –.

Column 28, Line 34 patent reads "µt" and should read – µL –.

UNITED STATES PATENT AND TRADEMARK OFFICE
CERTIFICATE OF CORRECTION

PATENT NO. : 5,698,696

DATED : 16 December 1997

INVENTOR(s) : Gilbert Marciniak; Richard A. Schnettler; Timothy A. Ayers; Damian J. Krysan

It is certified that error appears in the above-identified patent and that said Letters Patent is hereby corrected as shown below:

Column 28, Line 37 patent reads "mol arity" and should read – molarity –.

Column 29, Line 6 patent reads "DIYDRO" and should read – DIHYDRO –.

Column 29, Line 17 patent reads "trimethyihydroquinone" and should read – trimethylhydroquinone –.

Column 31, Lines 32 and 33 patent reads "dichloromethane" and should read – dichloro-methane –.

Column 31, Line 66 patent reads "slurtied" and should read – slurried –.

Column 44, Line 20 patent reads "exvivo" and should read – ex vivo –.

Column 45, Line 35 patent reads "grannulations" and should read – granulations –.

Column 46, Line 6 patent reads "may be also be" and should read – may also be –.

Column 47, Line 29 patent reads "moleties" and should read – moieties –.

Column 49, Line 38 patent reads "hydroxymethyi" and should read – hydroxymethyl –.

Column 49, Line 55 patent reads "by desired" and should read – by the desired – .

Column 50, Line 11 patent reads "racemic racemic" and should read – racemic –.

UNITED STATES PATENT AND TRADEMARK OFFICE
CERTIFICATE OF CORRECTION

PATENT NO. : 5,698,696

DATED : 16 December 1997

INVENTOR(s) : Gilbert Marciniak; Richard A. Schnettler; Timothy A. Ayers; Damian J. Krysan It is certified that error appears in the above-identified patent and that said Letters Patent is hereby corrected as shown below:

Column 54, Line 49 patent reads "benzolutah" and should read – benzofuran –.

Column 56, Line 36 patent reads "benzolutah" and should read – benzofuran –.

Column 57, Line 9 patent reads "(10)by" and should read – (10) by –.

Column 40, Line 30 patent reads "benzy! oxy" and should read – benzyloxy –.

Column 40, Line 51 patent reads "sazurated" and should read – saturated –.

Column 42, Line 13 patent reads "coiliris" and should read – collitis –.

Column 42, Line 33 patent reads "Wolffetal." and should read – Wolff et al. –.

Signed and Sealed this

Twenty-fourth Day of October, 2000

Attest:

Q. TODD DICKINSON

*Attesting Officer*  *Director of Patents and Trademarks*